(12) United States Patent
Pittock et al.

(10) Patent No.: US 11,061,027 B2
(45) Date of Patent: Jul. 13, 2021

(54) MATERIALS AND METHODS FOR EVALUATING AND TREATING CANCER

(71) Applicant: MAYO FOUNDATION FOR MEDICAL EDUCATION AND RESEARCH, Rochester, MN (US)

(72) Inventors: Sean J. Pittock, Rochester, MN (US); Thomas J. Kryzer, Mantorville, MN (US); Avi Gadoth, Givatayim (IL); Andrew McKeon, Rochester, MN (US); Vanda A. Lennon, Rochester, MN (US); James P. Fryer, Stewartville, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 42 days.

(21) Appl. No.: 16/334,978

(22) PCT Filed: Sep. 12, 2017

(86) PCT No.: PCT/US2017/051152
§ 371 (c)(1),
(2) Date: Mar. 20, 2019

(87) PCT Pub. No.: WO2018/063792
PCT Pub. Date: Apr. 5, 2018

(65) Prior Publication Data
US 2020/0041505 A1 Feb. 6, 2020

Related U.S. Application Data

(60) Provisional application No. 62/400,420, filed on Sep. 27, 2016.

(51) Int. Cl.
*G01N 33/564* (2006.01)
*G01N 33/574* (2006.01)

(52) U.S. Cl.
CPC ..... *G01N 33/564* (2013.01); *G01N 33/57423* (2013.01); *G01N 2800/28* (2013.01)

(58) Field of Classification Search
CPC ........... G01N 33/564; G01N 33/57423; G01N 2800/28
See application file for complete search history.

(56) References Cited

U.S. PATENT DOCUMENTS

2010/0267682 A1* 10/2010 Johri ............... A61K 31/00
514/171
2015/0268252 A1 9/2015 Svetlov et al.

FOREIGN PATENT DOCUMENTS

| CN | 1339494 | 3/2002 |
|---|---|---|
| WO | WO 2011/02155 | 1/2011 |
| WO | WO 2011/160096 | 12/2011 |

OTHER PUBLICATIONS

Ahmed et al. (Arch Surg. 2004 Vol. 139, p. 902-906). (Year: 2004).*
Extended European Search Report in European Application No. 17857186.5 dated Apr. 20, 2020, 15 pages.
Gadoth et al., "Microtubule Associated Protein (MAP) 1B: Antigen of PCA-2 IgG, Biomarker of Small-Cell Lung Carcinoma-related Paraneoplastic Neurological Autoimmunity," Neurology, 88(16Supp1):S41.007, Apr. 2017.
Gadoth et al., "Microtubule-associated protein 1 B: Novel paraneoplastic biomarker," Annals of neurology, 81(2):266-77, Feb. 2017.
Gupta et al., "Purkinje Cell Cytoplasmic Antibody (PCA-2)-related Chorea—Dystonia Syndrome," Tremor and Other Hyperkinetic Movements, 6:420, Sep. 2016.
Jarius and Wildemann, "'Medusa head ataxia': the expanding spectrum of Purkinje cell antibodies in autoimmune cerebellar ataxia. Part 3: Anti-Yo/CDR2, anti-Nb/AP3B2, PCA-2, anti-Tr/DNER, other antibodies, diagnostic pitfalls, summary and outlook," Journal of neuroinflammation, 12(1):168, Dec. 2015.
Rosenfeld and Dalmau, "Diagnosis and management of paraneoplastic neurologic disorders," Current treatment options in oncology, 14(4):528-38, Dec. 2013.
Waheed et al., "Double trouble: para-neoplastic anti-PCA-2 and CRMP-5-mediated small fibre neuropathy followed by chorea associated with small cell lung cancer and evolving radiological features," Case Reports, 2016:bcr2016215158, Aug. 2016.
Altschul et al.,"Gapped BLAST and PSI-BLAST: a new generation of protein database search programs," Nucleic 30 Acids Res., 25(17):3389-402, Sep. 1997.
Gadoth et al., "Microtubule Associated Protein (MAP) 1B; Antigen of PCA-2 IgG, Biomarker of Small-Cell Lung Carcinoma-related Paraneoplastic Neurological Autoimmunity," Neurology, 88(16):S41.007, Apr. 2017.
Gadoth et al., "Microtubule-Associated Protein IB; Novel Paraneoplastic Biomarker," Ann. Neurol., 8(12):266-77, Feb. 2017.
GenBank Accession No. AAA18904.1, "microtubule-associated protein 1B [*Homo sapiens*]," Jun. 10, 1994, 2 pages.
GenBank Accession No. CAM06633.1, "TPA: microtubule-associated protein 1B [*Homo sapiens*]," Jan. 18, 2007, 2 pages.
GenBank Accession No. CAM12311.1, "TPA: microtubule-associated protein 1B [*Homo sapiens*]," Jan. 15, 2007, 2 pages.
GenBank Accession No. P46821.2, "RecName: Full=Microtubule-associated protein 1B; Short=MAP-1B; Contains. RecName: Full=MAP1B heavy chain; Contains: RecName: Full=MAP1 light chain LC1," Feb. 28, 2018, 14 pages.
Greenlee et al., "Antibodies to cerebellar Purkinje cells in patients with paraneoplastic cerebellar degeneration and ovarian carcinoma," Ann. Neurol., 14(6):609-13, Dec. 1983.
Janus et al., "Antibodies to the inositol 1,4,5-trisphosphate receptor type 1 (ITPR1) in cerebellar ataxia" J. Neuroinflammation, 11:206, Dec. 2014.

(Continued)

*Primary Examiner* — Changhwa J Cheu
(74) *Attorney, Agent, or Firm* — Fish & Richardson P.C.

(57) ABSTRACT

This document provides methods and materials for detecting PCA-2-specific autoantibodies, which can be associated with paraneoplastic neurological disorders and cancers associated with PCA-2-specific autoantibodies.

15 Claims, 18 Drawing Sheets

Specification includes a Sequence Listing.

(56) References Cited

OTHER PUBLICATIONS

Janus et al., "Medusa head ataxia'; the expanding spectrum of Purkinje cell antibodies in autoimmune cerebellar ataxia. Part 3; Anti-Yo/CDR2, anti-Nb/AP3B2, PCA-2, anti-TR/DNER, other antibodies, diagnostic pitfalls, summary and outlook," J. Neuroinflammation, 12(168):1-22, Sep. 2015.

Jones et al., "Responses to and Outcomes of Treatment of Autoimmune Cerebellar Ataxia in Adults," JAMA Neurology,72(11):1304-12, Nov. 2015.

Lennon et al., "Immunization with neuronal nicotinic acetylcholine receptor induces neurological autoimmune disease" J. Clin. Invest.,111(6):907-13, Mar. 2003.

Lim and Halpain, "Regulated association of microtubule-associated protein 2 (MAP2) with Src and Grb2: evidence for MAP2 as a scaffolding protein," J. Biol. Chem., 275(27): 20578-87, Jul. 2000.

Parker et al., "Scheme for ranking potential HLA-A2 binding peptides based on independent binding of individual peptide sidechains," J. Immunol., 152(1):163-75, Jan. 1994.

PCT International Preliminary Report on Patentability in International Appln. No. PCT/US2017/051152 dated Apr. 11, 2019, 7 pages.

PCT International Search Report and Written Opinion in International Appln. No. PCT/US2017/051152 dated Dec. 18, 2017, 10 pages.

Sato-Yoshitake et al., "Microtubule-associated protein 1B: Molecular structure, localization, and phosphorylation-dependent expression in developing neurons," Neuron, 3(2):229-38, Aug. 1989.

Southwood et al., "Several Common HLA-DR Types Share Largely Overlapping Peptide Binding Repertoires," J. Immunol., 160(7):3363-73, Apr. 1998.

Vernino et al., "New Purkinje cell antibody (PCA-2): Marker of lung cancer—related neurological autoimmunity" Ann. Neurol., 47(3):297-305, 2000.

Yu et al., "CRMP-5 neuronal autoantibody: Marker of lung cancer and thymoma-related autoimmunity," Ann. Neurol., 49(2):146-54, Feb. 2001.

\* cited by examiner

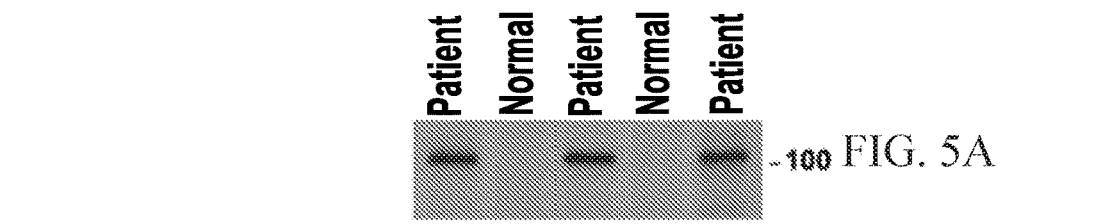

FIG. 5A

| patient | map 1b-1 | map 1b-2 | peptide 540-693 | map 1b-3 | map 1b-4 | map 1b-5 | map 1a-1 | map 1a-2 | map 1a-3 | map 1a-4 | map 1a-5 |
|---|---|---|---|---|---|---|---|---|---|---|---|
| 1 | pos | pos | pos | neg | pos | pos | pos | neg | neg | neg | neg |
| 2 | pos | neg | neg | neg | neg | neg | neg | neg | neg | neg | neg |
| 3 | pos | neg | neg | neg | neg | neg | neg | neg | neg | neg | neg |
| 4 | pos | pos | neg | neg | neg | *+/- | neg | neg | neg | neg | neg |
| 5 | pos | neg | pos | neg | neg | neg | neg | neg | neg | neg | neg |
| 6 | pos | pos | pos | pos | neg | *+/- | neg | neg | neg | neg | pos |
| 7 | pos | pos | pos | neg | neg | neg | neg | neg | neg | neg | neg |
| 8 | pos | pos | pos | neg | pos | neg | *+/- | neg | neg | neg | neg |
| 9 | pos | pos | pos | neg | *+/- | *+/-/+ | neg | neg | neg | neg | neg |
| 10 | pos | neg | pos | neg | neg | pos | neg | neg | neg | neg | neg |
| 11 | pos | neg | pos | neg | neg | neg | neg | neg | neg | neg | neg |
| 12 | pos | pos | pos | neg | pos | neg | neg | neg | nrg | neg | neg |
| 13 | pos | pos | pos | neg | neg | pos | *+/- | neg | neg | neg | neg |
| 14 | pos | neg | pos | neg | *+/- | neg | *+/- | neg | neg | neg | neg |
| 15 | pos | neg | neg | neg | neg | neg | neg | neg | neg | neg | neg |
| 16 | pos | neg | neg | neg | neg | neg | neg | neg | neg | neg | neg |
| 17 | pos | neg | neg | neg | neg | neg | neg | neg | neg | neg | neg |
| 18 | pos | *+/- | pos | neg | neg | neg | neg | neg | neg | neg | neg |
| 19 | pos | *+/- | pos | neg | neg | neg | neg | neg | neg | neg | neg |
| 20 | pos | *+/- | pos | neg | neg | neg | neg | neg | neg | neg | neg |
| 21 | pos | pos | pos | pos | pos | pos | pos | neg | neg | neg | pos |
| 22 | pos | neg | pos | neg | neg | neg | neg | pos | neg | neg | neg |
| 23 | pos | pos | pos | neg | neg | *+/- | *+/- | neg | neg | neg | neg |
| 24 | pos | neg | neg | neg | neg | neg | neg | neg | neg | neg | neg |
| 25 | pos | neg | neg | neg | neg | neg | neg | neg | neg | neg | neg |
| 26 | pos | neg | neg | neg | neg | neg | neg | neg | neg | neg | neg |
| 27 | pos | pos | pos | neg | pos | *+/- | neg | neg | neg | neg | neg |
| 28 | pos | pos | pos | neg | neg | neg | *+/- | neg | neg | neg | neg |
| 29 | pos | pos | pos | neg | neg | neg | neg | neg | *+/- | *+/- | neg |
| 30 | pos | pos | pos | neg | neg | neg | neg | neg | neg | neg | neg |
| 31 | pos | pos | neg | neg | neg | neg | neg | neg | neg | neg | neg |
| 32 | pos | neg | neg | neg | neg | neg | neg | neg | neg | neg | neg |
| 33 | pos | pos | pos | neg | neg | neg | *+/- | neg | *+/-/+ | neg | neg |
| 34 | pos | pos | pos | neg | neg | neg | neg | *+/- | pos | pos | neg |
| 35 | pos | neg | neg | neg | neg | neg | neg | neg | neg | neg | neg |
| 36 | pos | pos | pos | neg | neg | neg | neg | neg | neg | neg | neg |
| 37 | pos | neg | pos | neg | neg | neg | neg | neg | neg | neg | neg |
| 38 | pos | pos | pos | neg | neg | neg | neg | neg | neg | neg | neg |
| 39 | pos | neg | pos | neg | neg | neg | neg | neg | neg | neg | neg |
| 40 | pos | neg | neg | neg | neg | neg | neg | neg | neg | neg | neg |

Microtubule-associated protein 1B [Homo sapiens]

MATVVVEATEPEPSGSIANPAASTSPSLSHRFLDSKFYLLVVVGEIVTEEHLRRAIGNIELGIRSWDTN
LIECNLDQELKLFVSRHSARFSPEVPGQKILHHRSDVLETVVLINPSDEAVSTEVRLMITDAARHKLLV
LTGQCFENTGELILQSGSFSFQNFIEIFTDQEIGELLSTTHPANKASLTLFCPEEGDWKNSNLDRHNLQ
DFINIKLNSASILPEMEGLSEFTEYLSESVEVPSPFDI▒▒▒▒▒▒▒▒▒▒▒▒▒▒▒▒▒▒▒▒▒▒▒▒▒▒▒▒▒▒
▒▒▒▒MLINGGSE▒▒▒▒▒▒▒▒IRHLDRVDSILLTHIGDDNLPGINSMLQRKI▒▒▒▒▒▒▒▒▒TTNSDW
MKNLISPDLGVVFLNVPENLKNPEPNIKM▒▒▒▒▒▒▒FTLQYLNKLSMKPEPLFRSVGNTIDPVILFQK
MGVGKLE▒▒▒▒▒▒▒SSKEMQYFMQQWTGTNKDKAEFILPNGQEVDLPISYLTSVSSLIVWHPANPAEK
IIRVLFPGNSTQYN▒▒▒▒▒▒▒KHLDFLKQPLATQKDLTGQVPTPVVKQTKLKQRADSRESLKPAAKPL
PSKSVRKESKEETPEVTKVNHVE<u>KEEKVESKEKVMVKKDKEIKTETKESVTEKEVPSKEEPSPVKAEVA</u>
<u>EKQATDVKPKAAKEKTVKKETKVKPEDKKEEKEKPKKEVAKKEDK</u>TPIKKEEKPKKEEVKKEVKKEIKK
EEKKEPKKEVKKETPPKEVKKEVKKEEKKEVKKEEKEPKKEIKKLPKDAKKSSTPLSEAKKPAALKPKV
PKKEESVKKDSVAAGKPKEKGKIKVIKKEGKAAEAVAAAVGTGATTAAVMAAAGIAAIGPAKELEAERS
LMSSPEDLTKDFEELKAEEVDVTKDIKPQLELIEDEEKLKETEPVEAYVIQKEREVTKGPAESPDEGIT
TTEGEGECEQTPEELEPVEKQGVDDIEKFEDEGAGFEESSETGDYEEKAETEEAEEPEEDGEEHVCVSA
SKHSPTEDEESAKAEADAYIREKRESVASGDDRAEEDMDEAIEKGEAEQSEEEADEEDKAEDAREEEYE
PEKMEAEDYVMAVVDKAAEAGGAEEQYGFLTTPTKQLGAQSPGREPASSIHDETLPGGSESEATASDEE
NREDQP<u>EEETATSGYTQSTIEISSEPTPMDEMSTPRDVMSDETNNEETESPSQEEVNITKYESSLYSQE</u>
<u>YSKPADVTPLNGFSEGS</u>KTDATDGKDYNASASTISPPSSMEEDKFSRSALRDAYCSEVKASTTLDIKDS
ISAVSSEKVSPSKSPSLSPSPPSPLEKTPLGERSVNFSLTPNEIKVSAEAEVAPVSPEVTQEVVEEHCA
SPEDKTLEVVSPSQSVTGSAGHTPYYQSPTDEKSSHLPTEVIEKPPAVPVSFEFSDAKDENERASVSPM
DEPVPDSESPIEKVLSPLRSPPLIGSESAYESFLSADDKASGRGAESPFEEKSGKQGSPDQVSPVSEMT
STSLYQDKQEGKSTDFAPIKEDFGQEKKTDDVEAMSSQPALALDERKLGDVSPTQIDVSQFGSFKEDTK
MSISEGTVSDKSATPVDEGVAEDTYSHMEGVASVSTASVATSSFPEPTTDDVSPSLHAEVGSPHSTEVD
DSLSVSVVQTPTTFQETEMSPSK<u>EECPRPMSISPPDFSPKTAKSRTPVQDHRSEJSSMSIEPGQESPEQ</u>
<u>SLAMDFSRQSPDHFTVGAGVLHIIENGPTEVDYS</u>PSDMQDSSLSHKIPPMEEPSYTQDNDLSELISVSQ
VEASPSTSSAHTPSQIASPLQEDTLSDVAPPRDMSLYASLTSEKVQSLEGEKLSPKSDISPLTPRESSP
LYSPTFSDSTSAVKEKTATCHSSSSPPIDAASAEPYGFRASVLFDTMQHHLALNRDLSTPGLEKDSGGK
TPGDFSYAYQKPEETTRSPDEEDYDYESYEKTTRTSDVGGYYYEKIERTTKSPSDSGYSYETIGKTTKT
PEDGDYSYEIIEKTTRTPEEGGYSYDISEKTTSPPEVSGYSYEKTERSRRLLDDISNGYDDSEDGGHTL
GDPSYSYETTEKITSFPESEGYSYETSTKTTRTPDTSTY<u>CYETAEKITPRTPQASTYSYETSDLCYTAEK</u>
<u>KSFSEAROLVDLCLVSSCEYKHPKTELSESFINPNPLEWFASEEPTEESE</u>KPLTQSGGAPPPPGGKQQG
RQCDETPPTSVSESAPSQT▒▒▒▒▒▒▒▒▒DANIDSEDESETIPTDKTVTYKHMDPPPAPVQDR
SPSPRHPDVSMVDPEALAIEQNLGKALKKDLKEKTKTKKPGTKTKSSSPVKKSDGKSKPLAASPKPAGL
KESSDKVSRVASPKKKESVEKAAKPTTTPEVKAARGEEKDKETKNAANASASKSAKTATAGPGTTKTTK
SSAVPPGLPVYLDLCYIPNHSNSKNVDVEFFKRVRS▒▒▒▒▒▒▒▒▒AE▒▒▒▒▒▒▒▒▒▒▒▒▒▒▒SN
M▒▒▒▒▒▒▒SEVMREWYQETHEKQQDLNIM▒▒▒▒▒▒▒▒▒▒▒▒▒L

FIG. 9

Microtubule-associated protein 1A [Homo sapiens]

MDGVAEFSEYVSETVDVPSPFDL████████████████████████ILVDGGSD█
██████VRHLDRIDSVLLTHIGADNLPGINGLLQRKV█████████SSYSDWVKNLISPELGVVFFN
VPEKLRLPDASRKA████████LTLQHLNRLGIQAEPLYRVVSNTIEPLTLFHKMGVRLD██████
DSKEMQFLMQKWAGNSKAKTGIVLPNGKEAEISVPYLTSITALVVWLPANPTEKIVRVLFPGNAPQNK█
████████RHLDFLRYPVATQKDLASGAVPTNLKPSKIKQRADSKESLKATTKTAVSKLAKREEVVEEGA
KEARSELAKELAKTEKKAKESSEKPPEKPAKPERVKTESSEALKAEKRKLIKDKVGKKHLKEKISKLEE
KKDKEKKEIKKERKELKKDEGRKEEKKDAKKEEKRKDTKPELKKISKPDLKPFTPEVRKTLYKAKVPGR
VKIDRSRAIRGEKELSSEPQTPPAQKGTVPLPTISGHRELVLSSPEDLTQDFEEMKREERALLAEQRDT
GLGDKPFPLDTAEEGPPSTAIQGTPPSVPGLGQEEHVMKEKELVPEVPEEQGSKDRGLDSGAETEEEKD
TWEEKKQREAERLPDRTEAREESEPEVREDVIEKAELEEMEEVHPSDEEEEDATKAEGFYQKHMQEPLK
VTPRSREAFGGRELGLQGKAPEKETSLFLSSLTTPAGATEHVSYIQDETIPGYSETEQTISDEEIHDEP
EERPAPPRFHTSTYDLPGPEGAGPFEASQPADSAVPATSGKVYGTPETELTYPTNIVAAPLAEEEHVSS
ATSITECDKLSSFATSVAEDQSVASLTAPQTEETGKSSLLLDTVTSIPSSRTEATQGLDYVPSAGTISP
TSSLEEDKGFKSPPCEDFSVTGESEKRGEIIGKGLSGERAVEEEEEETANVEMSEKLCSQYGTPVFSAP
GHALHPGEPALGEAEERCLSPDDSTVKMASPPPSGPPSATHTPFHQSPVEEKSEPQDFQEADSWGDTKR
TPGVGKEDAAEETVKPGPEEGTLEKEEKVPPPRSPQAQEAPVNIDEGLTGCTIQLLPAQDKAIVFEIME
AGEPTGPILGAEALPGGLRTLPQEPGKPQKDEVLRYPDRSLSPEDAESLSVLSVPSPDTANQEPTPKSP
CGLTEQYLHKDRWPEVSPEDTQSLSLSEESPSKETSLDVSSKQLSPESLGTLQFGELNLGKEEMGHLMQ
AEDTSHHTAPMSVPEPHAATASPPTDGTTRYSAQTDITDDSLDRKSPASSFSHSTPSGNGKYLPGAITS
PDEHILTPDSSFSKSPESLPGPALEDIAIKWEDKVPGLKDRTSEQKKEPEPKDEVLQQKDKTLEHKEVV
EPKDTAIYQKDEALHVKNEAVKQQDKALEQKGRDLEQKDTALEQKDKALEPKDKDLEEKDKALEQKDKI
PEEKDKALEQKDTALEQKDKALEPKDKDLEQKDRVLEQKEKIPEEKDKALDQKVRSVEHKAPEDTVAEM
KDRDLEQTDKAPEQKHQAQEQKDKVSEKKDQALEQKYWALGQKDEALEQNIQALEENHQTQEQESLVQE
DKTRKPKMLEEKSPEKVKAMEEKLEALLEKTKALGLEESLVQEGRAREQEEKYWRGQDVVQEWQETSPT
REEPAGEQKELAPAWEDTSPEQDNRYWRGREDVALEQDTYWEELSCERKVWFPHELDGQGAPPHYTEER
ESTFLDEGPDDEQEVPLREHATRSPWASDFKDFQESSPQKGLEVERWLAESPVGLPPEEEDKLTRSPFE
IISPPASPPEMVGQRVPSAPGQESPIPDPKLMPHMKNEPTTPSWLADIPPWVPKDRPLPPAPLSPAPGP
PTPAPESHTPAPFSWGTAEYDSVVAAVQEGAAELEGGPYSPLGKDYRKAEGEREEGRAEAPDKSSHSS
KVPEASKSHATTEPEQTEPEQREPTPYPDERSFQYADIYEQMMLTGLGPACPTREPPLGAAGDWPPCLS
TKEAAAGRNTSAEKELSSPISPKSLQSDTPTFSYAALAGPTVPPRPEPGPSMEPSLTPPAVPPRAPILS
KGPSPPLNGNILSCSPDRRSPSPKESGRSHWDDSTSDSELEKGAREQPEKEAQSPSPPHPIPMGSPTLW
PETEAHVSPPLLSHLSPARPSLDPPASAPGFSSLQPAEPQLPSPAEPPSAPCGSLAPSGLRALALAPGP
PTRTRHDEYLEVTKAPSLDSSLPQLPSPSSPGAPLLSNLPRPASPALSEGSSSEATTPVISSVAERFSP
SLEAAEQESGELDPGMEPAAHSLWDLTPLSPAPPASLDLALAPAPSLPGDMGDGILPCHLECSEAATEK
PSPFQVPSEDCAANGPTETSPNPPGPAPAKAENEEAAACPAWERGAWPEGAERSSRPDTLLSPEQPVCP
AGGSGGPPSSASPEVEAGPQGCATEPRPHRGELSPSFLNPPLPPSIDDRDLSTEEVRLVGRGGRRRVGG
PGTTGGPCPVTDETPPTSASDSGSSQS█████████████EAALDSDEDGDFLPVDKAGGVSGTHH
PRPGHDPPPLPQPDPRPSPPRPDVCMADPEGLSSESGRVERLREKEKVQGRVGRRAPGKAKPASPARRL
DLRGKRSPTPGKGPADRASRAPPRPRSTTSQVTPAEEKDGHSPMSKGLVNGLKAGPMALSSKGSSGAPV
YVDLAYIPNHCSGKTADLDFFRRVRA████████NG██████████████████ENL████████
TEVTREWYQQTHEQQQQLNVL███████████████F

FIG. 10

| Pt No/Sex/Age | Clinical syndrome | Additional antibodies | MAP1B pos | Additional MAPs pos | Cancer/time of diagnosis | MRI brain | MRI spine | CSF WCC*/Pro/O CBs/ IgG I | Treatment /response |
|---|---|---|---|---|---|---|---|---|---|
| 1/f/69 | LES, Brain stem encephalitis, nausea, vomiting, dysautonomia | CCN,CCPQ | Yes | No | SCLC/prior | NA | NA | NA | NA |
| 2/f/82 | Sensory motor neuropathy and ataxia | ARBi, GAD-65 | NA | NA | NA | NA | NA | NA | NA |
| 3/f/72 | Sensory motor neuropathy, ataxia and LES | CCPQ | Yes | No | SCLC/follow | NA | NA | NA | Steroids/NA |
| 4/f/60 | Limbic encephalitis, seizures and myelitis | CCPQ, Alpha3, GAD 65 | Yes | No | SCLC/follow | HC lesion | NA | NA | NA |
| 5/f/62 | ataxia | GAD 65, CCN, CCPQ | Yes | No | NSCLC/follow | NL | NA | NA | NA |
| 6/m/66 | Sensory neuropathy, ataxia and hand dystonia | Amphiphysin | NA | NA | Renal */prior | NA | NA | NL | Chemo/NA |
| 7/f/68 | Cerebellar | | NA | NA | SCLC/follow | NA | NA | Lymphocytosis ** | Chemo/Yes |
| 8/f/73 | Ataxia and sensory neuropathy | | Yes | No | Breast */follow | SVD | NL | 1/37/1/12 | CTX/Yes |
| 9/f/68 | Painful neuropathy | | NA | NA | Skin SQ/prior | NA | NA | NA | NA |
| 10/f/74 | Diffuse pain | Alpha-3 | NA | NA | SCLC/prior | NA | NL | NL* | Chemo/NA |
| 11/f/49 | Painful peripheral neuropathy | CRMP-5, GAD-65, CCN | NA | NA | Pancreas SCC/follow | NA | NA | NA | Res/NA |
| 12/f/76 | NA | NA | NA | NA | NA | NA | NA | NA | NA |
| 13/m/44 | Ataxia and autonomic dysfunction | CRMP-5, alpha-3 | NA | NA | SCLC/follow | NA | NA | NA | NA |
| 14/f/74 | Peripheral neuropathy, LEMS and encephalopathy | CCPQ, GAD-65 | Yes | No | SCLC/follow | NA | NA | NA | NA |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/OCBs/ IgG I | Treatment /response |
|---|---|---|---|---|---|---|---|---|---|
| 15/m/77 | Sensory motor peripheral neuropathy and dysarthria | CRMP-5, GAD-65, CCPQ, CCN | Yes | NA | SCLC/follow | NA | NA | 18/97/NA/I** | Chemo/yes |
| 16/f/39 | myelopathy | GAD-65 | NA | NA | Breast */prior | Demyelination | NA | 0/NL/3/I** | Chemo+res/NA |
| 17/m/77 | Encephalopathy, cerebellar and autonomic | GAD-65 | Yes | NA | Prostate */prior | Meningeal enhancement | NL | 75/203/2/1.29 | Steroids/Yes |
| 18/m/80 | Limbic encephalitis, motor weakness | CRMP-5, STR, GAD-65, VGKC | Yes | NA | NA | NA | NA | I**/I**/NA/NA | NA |
| 19/m/88 | LEMS and encephalopathy | CCPQ, CCN | Yes | MAP1B-2 | SCLC/at | NA | NA | NA | NA |
| 20/f/61 | NA | CCPQ, GAD-65 | Yes | NA | NA | NA | NA | NA | NA |
| 21/m/73 | Limbic encephalitis | | Yes | No | SCLC/prior | NA | NA | NA | NA |
| 22/m/70 | Left extremities weakness and paresthesia | | Yes | NA | NSCLC/at | NA | NA | NA | Radiation/N.A |
| 23/f/72 | Bilateral optic neuropathy and peripheral neuropathy | CRMP-5 | Yes | NA | SCLC/prior | Enhancement of optic nerves | NA | 162/84/NA/NA | Steroids/Yes |
| 24/m/72 | Suspected LEMS | CCPQ, GAD-65 | Yes | NA | SCLC/follow | NA | NA | NA | NA |
| 25/f/64 | Painful sensory neuropathy | VGKC, Amphi | Yes | NA | SCLC/follow | NA | NA | NA | NA |
| 26/m/59 | Cerebellar ataxia dysarthria and blurred vision | CCPQ | Yes | NA | NA | NA | NA | NA | NA |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/O CBs/ IgG I | Treatment /response |
|---|---|---|---|---|---|---|---|---|---|
| 27/m/72 | Diplopia and peripheral neuropathy with weakness | | Yes | No | SCLC/at | NL | NA | NA | Chemo/NA |
| 28/m/62 | Peripheral neuropathy | CCN, CCPQ | Yes | NA | SCLC/follow | NA | NA | NA | NA |
| 29/f/64 | Pan cerebellar | CRMP-5 | Yes | NA | SCLC/prior | Cerebellar atrophy | NA | NA | Chemo+rad/No |
| 30/m/75 | Limbic encephalitis | ANNA-1, CRMP-5 | Yes | NA | NSCLC/follow | Temporal and parietal lobes signal abnormalities | NA | 1/58/1/I | NA |
| 31/m/77 | Ataxia | GAD-65, VGKC | Yes | NA | Lung SQ/at | NA | NA | NA | Chemo+rad/NA |
| 32/f/81 | Lethargy and generalized weakness | | No | | SCLC/follow | NA | NA | NA | NA |
| 33/m/62 | NA | ANNA-1, CCPQ, VGKC | Yes | NA | NA | NA | NA | NA | NA |
| 34/m/66 | NA | CRMP-5, CCPQ | Yes | MAP1B-2 | NA | NA | NA | NA | NA |
| 35/f/66 | Limbic encephalitis, ataxia, sensory neuropathy, chorea, decreased vision | CRMP-5, Amphi | Yes | NA | SCLC/follow | T2 hyperintensities in the basal ganglia | NA | 6/39/NA/NA | Chemo+steroids /stable† |
| 36/f/66 | Sensory neuropathy and spasms | ANNA-1 | Yes | NA | No | NL | NA | NA | Steroids/No |
| 37/m/69 | Ataxia and diplopia, abnormal eye movements | ANNA-1, GAD-65 | Yes | NA | SCLC/follow | SVD | NA | NA | No/NA |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/OCBs/ IgG I | Treatment /response |
|---|---|---|---|---|---|---|---|---|---|
| 38/f/65 | Sensory motor polyneuropathy | CRMP-5 | Yes | NA | NA | NA | NA | NA | NA |
| 39/m/71 | Ataxia + sensory motor peripheral neuropathy | CRMP-5 | Yes | NA | SCLC/follow | NA | NA | 10/NA/NA/NA | NA |
| 40/f/61 | Seizures and transverse myelitis | | Yes | NA | No | NL | NA | I*/NA/I*/NA | NA |
| 41/f/64 | Ataxia | STR, ANNA-1, CRMP-5 | Yes | NA | SCLC/prior | NA | NA | NA | Chemo+rad/NA |
| 42/m/75 | Ataxia and bilateral optic neuritis | CRMP-5, ANNA-1, CCN | Yes | NA | SCLC/at | SVD | NA | 4/83/1/NA | Chemo, steroids, CTX/Yes |
| 43/m/70 | Widespread pain | | NA | NA | SCLC/follow | NA | NA | NA | Chemo/Yes |
| 44/f/79 | Limbic encephalitis | ANNA-1 | Yes | NA | No | Temporal hyperintencities and hippocampal atrophy | NA | 1/54/NA/NA | No |
| 45/m/73 | Ataxia + blurred vision | GAD-65 | Yes | NA | SCLC/NA | NL | NA | No | NA |
| 46/f/73 | Ptosis and eye deviation | | NA | NA | NA | NA | NA | NA | Steroids, IVIG, PLX/No |
| 47/m/75 | Gastrointestinal dysmotility | | NA | NA | NCSLC | NA | NA | NA | NA |
| 48/f/57 | Seizures and aphasia | CCPQ, AGNA-1 | NA | NA | NA | NA | NA | NA | NA |
| 49/f/65 | Ataxia, dysarthria and diplopia | CRMP-5 | Yes | NA | SCLC/follow | Atrophy | NA | 2/60/3/0.6 | Chemo, steroids/stable† |
| 50/f/59 | Ataxia | ANNA-1 | Yes | NA | SCLC/at | NA | NA | NA | Chemo, steroids/No |
| 51/m/80 | Sensory motor peripheral neuropathy | | Yes | MAP1B-2 | Lung */follow | NA | NA | NA | NA |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/OCBs/ IgG I | Treatment /response |
|---|---|---|---|---|---|---|---|---|---|
| 52/m/63 | Peripheral motor neuropathy, visual disturbance and sensory level | CRMP-5, CCPQ, CCN | Yes | NA | SCLC/prior | NA | NA | NA | PLX/No |
| 53/m/74 | NA | NA | NA | NA | NA | NA | NA | NA | NA |
| 54/f/81 | Sensory motor neuropathy/radiculopathy, ataxia, seizures | | Yes | MAP1B-2, 4, 5, MAP1A-1 | No | NOS/SVD | NA | 6/66/7/0.65 | CTX/steroids/Yes |
| 55/f/57 | NA | VGKC | Yes | No | NA | NA | NA | NA | NA |
| 56/f/68 | Confusion and paranoia | ANNA-1 | Yes | NA | SCLC/NA | diffuse white matter abnormalities | NA | NL/NL/NA/NA | Chemo/Yes |
| 57/m/53 | Cerebellar | CRMP-5 | Yes | NA | NA | NA | NA | NA | NA |
| 58/m/52 | Ataxia and sensory neuropathy | CRMP-5 | Yes | NA | No | mild atrophy | hyperintense lesions with enhancement | 4/54/I/NA | Steroids/Yes |
| 59/m/73 | Limbic encephalitis, gait unsteadiness | ANNA-1 | Yes | NA | SCLC/follow | atrophy and scattered T2 white matter hyperintensities | mild contrast prominence in the inferior thoracic spine | 8/112/NA/NA | Chemo, steroids/Yes |
| 60/m/69 | Ataxia, transverse myelitis | | Yes | MAP1B-2, 4, 5, MAP1A-3, 5 | SCLC/NA | NA | subtle changes on cord | NA | NA |
| 61/f/84 | Subacute cognitive decline | ANNA-1, Amphi, VGKC | NA | NA | No | NA | NA | NA | NA |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/O CBs/ IgG I | Treatment /response |
|---|---|---|---|---|---|---|---|---|---|
| 62/f/51 | NA | NA | NA | NA | NA | NA | NA | NA | NA |
| 63/m/74 | NA | CCN, CCPQ, | Yes | MAP1B-2, 4 | NA | NA | NA | NA | NA |
| 64/f/53 | Cerebellar ataxia and encephalopathy | GAD-65 | Yes | MAP1A-2 | SCLC/follow | NA | NA | NA | Chemotherapy/s table† |
| 65/m/41 | Sensory ataxia with cerebellar involvement | GABA-B, CCN | Yes | NA | No | NA | NA | NA | NA |
| 66/f/63 | NA | Alpha-3 | Yes | MAP1B-2 | NA | NA | NA | NA | NA |
| 67/f/82 | Peripheral neuropathy | | Yes | No | No | NA | NA | NA | NA |
| 68/f/67 | Motor axonal neuropathy | CRMP-5 | Yes | NA | SCLC/follow | NA | NL | NA | NA |
| 69/f/32 | NA | | NA | NA | No | multiple lesion | NA | NA | NA |
| 70/m/61 | Sensory motor peripheral neuropathy, clumsiness of hands and ataxia | CCPQ, VGKC | NA | NA | SCLC/follow | NOS | patchy areas of increased T2 signal with enhanceme nt, meningeal enhanceme nt. | 22/102/3/1.4 5 | Chemo+rad/Yes |
| 71/m/67 | LEMS | CCPQ, ARBi | NA | NA | NA | NA | NA | NA | NA |
| 72/m/74 | Weakness of lower extremities and general weakness | | Yes | MAP1B-2, 5 | Lung SQ/at | NA | NA | NA | Chemo+rad/NA |
| 73/m/65 | Demyelinating sensory motor peripheral neuropathy | CCPQ | Yes | No | SCLC/prior | NA | NA | NA | NA |
| 74/m/68 | NA | CRMP-5, ANNA-1 | Yes | NA | NA | NA | NA | NA | NA |
| 75/m/74 | Vision loss - retinopathy | | Yes | No | Liver adenocarcin oma/follow | NA | NA | NA | Chemo/No |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/O CBs/ IgG I | Treatment /response |
|---|---|---|---|---|---|---|---|---|---|
| 76/m/57 | NA | CCPQ, CCN | Yes | MAP1B-2, 4 | NA | NA | NA | NA | NA |
| 77/m/75 | NA | | NA | NA | NA | NA | NA | NA | NA |
| 78/m/66 | Gait ataxia and leg weakness | CRMP-5, GAD-65 | Yes | NA | SCLC/follow | NA | NA | NA | NA |
| 79/m/73 | NA | CCPQ, CCN | Yes | NA | NA | NA | NA | NA | NA |
| 80/m/64 | NA | ANNA-1 | Yes | NA | NA | NA | NA | NA | NA |
| 81/m/69 | NA | | Yes | MAP1B-5 | NA | NA | NA | NA | NA |
| 82/m/62 | Sensory motor peripheral neuropathy, cognitive decline, hallucinations, | | Yes | NA | Lung */follow | SVD | NA | NL/NL/I/NA | PLX,CPT/Yes |
| 83/f/67 | Dysautonomia | CRMP-5 | Yes | NA | Breast *, ovary */prior | NA | NA | NA | NA |
| 84/m/71 | NA | | Yes | MAP1B-2 | NA | NA | NA | NA | NA |
| 85/m/57 | Paresthesia, small fiber neuropathy, chorea | CRMP-5, alpha-3 | Yes | NA | SCLC/follow | NL | NA | NL/NL/NL/NA | Chemo, steroids/Yes |
| 86/m/83 | Confusion and delirium | | Yes | MAP1B-2, MAP1A-3 | Prostate */follow | Atrophy | NA | 149/I/NA/NA | Res/minimal ‡ |
| 87/f/74 | NA | CRMP-5, CCN | Yes | NA | NA | NA | NA | NA | NA |
| 88/f/71 | NA | | Yes | MAP1B-2 | NA | NA | NA | NA | NA |
| 89/m/82 | Sensory motor peripheral neuropathy | GAD-65 | Yes | MAP1B-2 | Lung */NA | NA | NA | NA | Chemo, PLX/stable† |
| 90/m/27 | Vision loss - retinopathy | GAD-65, alpha-3, CCN, VGKC | Yes | NA | Ewing sarcoma/follow | NA | NA | NA | RTX+steroids |
| 91/m/49 | Ataxia and hand clumsiness | VGKC, alpha-3, CCN | NA | NA | NSCLC/follow | NA | NA | NA | NA |
| 92/m/89 | Sub-acute myelopathy, gait disturbance | STR | Yes | MAP1B-2, MAP1A-3 | Nasopharyngeal adenocarcinoma/at | non enhancing lesion | NA | NA | Steroids/Yes |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/O CBs/ IgG I | Treatment /response |
|---|---|---|---|---|---|---|---|---|---|
| 93/m/72 | Progressive weakness | | Yes | MAP1B-2, MAP1A-3, 4 | No | NA | NA | NA | NA |
| 94/f/72 | Peripheral neuropathy and ataxia | ANNA-1, CRMP-5, CCPQ | Yes | NA | SCLC/NA | cerebellar atrophy | NA | NA | NA |
| 95/f/50 | Stiffness and generalized pain | | Yes | No | Lung adenocarcinoma/prior | NL | metastasis | NA | Chemo, steroids/No |
| 96/f/24 | Pseudo-obstruction | ANNA-1, CRMP-5, STR | Yes | MAP1B-2 | No | NA | NA | NA | NA |
| 97/m/58 | Inflammatory myopathy | STR, ARBi | Yes | No | No | NA | Thoracic spine lesion-T10-11 bad disc bulge. | NA | Steroids/Yes |
| 98/m/70 | Limbic encephalitis | | NA | NA | SCLC/follow | NA | NA | NA | NA |
| 99/m/76 | Ataxia and Oscillopsia | CRMP-5, STR, ARBi | Yes | NA | SCLC/follow | NA | NA | 74/86/NA/NA | NA |
| 100/m/68 | Sensory motor peripheral neuropathy | | Yes | No | No | SVD | NL | 2/50/NA/NA | NA |
| 101/f/67 | Limbic encephalitis, seizures | GABA-B, AMPA, CCN | Yes | NA | Lung */NA | NA | NA | NA | Chemo/NA |
| 102/f/60 | NA | CCN, CCPQ, GABA-B | Yes | NA | NA | NA | NA | NA | NA |
| 103/f/79 | Memory decline and headache | | Yes | MAP1B-2 | No | NL | NA | NA | NA |
| 104/f/75 | NA | GAD-65 | Yes | NA | NA | NA | NA | NA | NA |
| 105/f/81 | Diplopia and ptosis | | Yes | MAP1B-2, 4 | SCLC/follow € | NA | NA | NA | NA |
| 106/f/57 | Bilateral optic neuritis and uveitis, limb numbness | | Yes | MAP1B-2, 5 | SCLC/follow | Swelling of the optic nerves | NA | NA | Chemo/Yes |

FIG. 10 (cont.)

| Pt No/Sex/Age | Clinical syndrome | Additional antibodies | MAP1B pos | Additional MAPs pos | Cancer/time of diagnosis | MRI brain | MRI spine | CSF WCC*/Pro/OCBs/ IgG I | Treatment /response |
|---|---|---|---|---|---|---|---|---|---|
| 107/f/63 | Memory decline | AGNA-1, CCPQ | Yes | NA | Thymoma | NL | NA | NA | NA |
| 108/f/70 | NA | | No | | NA | NA | NA | NA | NA |
| 109/m/32 | NA | | Yes | NA | NA | NA | NA | NA | NA |
| 110/m/74 | NA | | Yes | MAP1B-2, 5 | NA | NA | NA | NA | NA |
| 111/f/62 | Hemi Chorea | CRMP-5, STR, ARBi, AMPA | NA | NA | Thymoma | NL | NA | NA | NA |
| 112/f/22 | Paresthesia in arms | | NA | NA | Large cell anaplastic lymphoma/prior | NL | NL* (brachial plexitis) | NA | NA |
| 113/m/69 | Ataxia and involuntary movements in all limbs and mouth | CCN | Yes | No | Lung */follow ϕ | Caudate atrophy | NA | NA | Steroids, PLX/Yes |
| 114/f/63 | Myelopathy, sensory neuropathy and visual disturbance | CRMP-5 | Yes | NA | Lung* /NA ϕ | Mild volume loss | NL | NL/I/NA/NA | Steroids, PLX, IVIG/No |
| 115/m/74 | Flaccid weakness, diplopia and depression | CRMP-5 | Yes | NA | No ¥ | NL | NL | 33/43/NA/NA | PLX, IVIG/No |
| 116/m/65 | Confusion, altered mental status and diplopia | ANNA-1, CRMP-5, GAD-65 | Yes | NA | No ¥ £ | Some T2 changes around the aqueduct. | NL | 10/47//NA/NL | IVIG/No |
| 117/m/71 | Ataxia, numbness in all limbs | | Yes | NA | No ¥ | NOS | NA | NA | NA |
| 118/m/70 | Altered mental status | | Yes | NA | NSCLC/at | NL | NA | NA | Chemo/NA |

MATERIALS AND METHODS FOR EVALUATING AND TREATING CANCER

CROSS-REFERENCE TO RELATED APPLICATIONS

This application claims priority to U.S. Application Ser. No. 62/400,420, filed on Sep. 27, 2016. The disclosure of the prior application is considered part of the disclosure of this application, and is incorporated in its entirety into this application.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310159_414USPC_SEQUENCE_LISTING.txt. The text file is 45.7 KB, was created on Mar. 13, 2019, and is being submitted electronically via EFS-Web.

BACKGROUND

1. Technical Field

This document relates to methods and materials for evaluating and treating paraneoplastic neurological disorders and cancers associated with Purkinje cell antibody-type 2 (PCA-2)-specific autoantibodies. For example, this document relates to methods and materials for using microtubule associated protein 1B (MAP1B) polypeptides and fragments thereof to detect the presence or absence of PCA-2-specific autoantibodies.

2. Background Information

Neural-restricted autoantibodies are emerging as serum biomarkers of acquired neurological disorders, both idiopathic and paraneoplastic. PCA-2 was described in 2000 as an IgG biomarker of paraneoplastic neurologic autoimmunity initiated by small-cell lung carcinoma (SCLC), with an ~280-kDa onconeural cytoplasmic antigen expressed in central and peripheral neural tissues and SCLC cells (Vernino et al., *Ann. Neurol.*, 47:297-305 (2000)). The autoantibody was named PCA-2 to distinguish it from a biomarker of ovarian and breast cancer-related cerebellar degeneration, PCA-1 (AKA anti-Yo; Greenlee et al., *Ann. Neurol.*, 14:609-13 (1983)).

SUMMARY

This document provides methods and materials for detecting paraneoplastic neurological disorders and/or cancers associated with PCA-2-specific autoantibodies as well as methods and materials for treating paraneoplastic neurological disorders and/or cancers associated with PCA-2-specific autoantibodies (e.g., neuroendocrine tumors).

As described herein, MAP1B is the antigenic target of a paraneoplastic neurological disorders and/or cancers associated with PCA-2-specific autoantibodies, which serve as a strong positive predictor of small-cell lung carcinoma and a biomarker for paraneoplastic neurological disorders with a diversity of neurological manifestations. The detection of PCA-2-specific autoantibodies (also referred to as MAP1B-specific autoantibodies herein) can be used to support the diagnosis of a paraneoplastic neurological disorders and cancers associated with PCA-2-specific autoantibodies. MAP1B is highly expressed in both developing neurons and in neuroendocrine tumors (e.g., SCLC), and can be targeted for the treatment of paraneoplastic neurologic disorders.

In general, one aspect of this document features a method of detecting the presence or absence of a PCA-2-specific autoantibody in a biological sample from an individual. The method includes, or consists essentially of, contacting a biological sample from an individual with a MAP1B polypeptide or fragment thereof to form a MAP1B-PCA-2-specific autoantibody complex if the biological sample contains said PCA-2-specific autoantibody, and detecting the presence or absence of the complex. The presence of the PCA-2-specific autoantibody in the biological sample can be associated with a paraneoplastic neurological disorder or a cancer associated with PCA-2-specific autoantibodies in the individual. The paraneoplastic neurological disorder can be encephalitis/encephalopathy, seizures, sleep disorders, cerebellar dysfunction/cerebellar degeneration/cerebellar ataxia, optic neuropathy, retinopathy, movement disorders/non voluntary movements, eye movement abnormalities, peripheral neuropathy, autonomic dysfunction, neuromuscular junction syndromes, Lambert-Eaton myasthenic syndrome (LEMS), Cushing syndrome, syndrome of inappropriate antidiuretic hormone secretion (SIADH), paraneoplastic cerebellar degeneration, encephalomyelitis, limbic encephalitis, brainstem encephalitis, opsoclonus myoclonus ataxia syndrome, or polymyositis. In some embodiments, the paraneoplastic neurological disorder can be LEMS. The cancer can be small-cell lung cancer (SCLC), renal carcinoma, squamous cell skin carcinoma, extrapulmonary small-cell carcinoma (EPSCC), prostate adenocarcinoma, primary intrahepatic cholangiocarcinoma, Ewing sarcoma, nasopharyngeal carcinoma, lymphoma, large cell neuroendocrine carcinoma of the lung (LCNEC), gastroenteropancreatic neuroendocrine tumors (GEP-NET), pituitary tumors, thyroid tumors, or medullary carcinoma. In some embodiments, the cancer can be SCLC. The method also can include performing a Western blot to detect the complex. The method also can include detecting the presence of the complex or detecting the absence of the complex. The biological sample can be serum, plasma, cerebrospinal fluid, or blood.

In another aspect, this document features a kit including a MAP1B polypeptide or fragment thereof and instructions for using the MAP1B polypeptide to detect a PCA-2-specific autoantibody in an individual. The kit can be used to diagnose the presence or absence of a paraneoplastic neurological disorder or a cancer associated with PCA-2-specific autoantibodies in an individual. The kit also can include a monoclonal antibody having specific binding affinity for a MAP1B polypeptide or fragment thereof. The kit also can include a PCA-2-specific autoantibody.

In another aspect, this document features a method of treating an individual having a paraneoplastic neurological disorder associated with PCA-2-specific autoantibodies. The method includes, or consists essentially of, identifying an individual as having a paraneoplastic neurological disorder associate with PCA-2-specific autoantibodies, and administering an immunomodulatory agent to said individual. The step of identifying an individual as having a paraneoplastic neurological disorder associate with PCA-2-specific autoantibodies can include contacting a biological sample from the individual with a MAP1B polypeptide or fragment thereof to form a MAP1B-PCA-2-specific autoantibody complex if said biological sample contains the PCA-2-specific autoantibody, and detecting the presence of the complex. The immunomodulatory agent can include a corticosteroid. The immunomodulatory agent can include cyclophosphamide. The immunomodulatory agent can include tacrolimus.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 5A-5B shows recombinant western blot screening of sera for binding to different Map1B and MAP1A fragments. A) A common band (~110 kDa by reference to molecular weight standards) was revealed by IgG in patients' sera (lanes 1, 2 and 3), but not by IgG in control human sera (lanes 4 and 5) when screening MAP1B fragment 1 recombinant protein on western blot. B) Recombinant MAP1B and MAP1A protein fragments probed by western blot with sera of 40 individual PCA-2-positive patients. IgG in all were reactive with MAP1B fragment 1 (polypeptide 1-666); 50% bound to fragment 2. Green=positive; yellow=moderately reactive; orange=equivocally reactive; red=negative. Western blot with a synthetic peptide comprising the overlap region of MAP1B fragment 1 and MAP1B fragment 2, revealed that residues 540-693 constituted a major B cell epitope (bound IgG in 27 of 40 patients' sera).

FIG. 8 shows the amino acid sequence (SEQ ID NO:1) of a human microtubule-associated protein 1B (MAP1B). Underlined and highlighted residues represent overlap between fragments. Highlighted residues represent regions of homology of 8 or more amino acids between MAP1B and MAP1A.

FIG. 9 shows the amino acid sequence (SEQ ID NO:2) of a human microtubule associated protein 1A (MAP1A). Underlined and highlighted residues represent overlap between fragments. Highlighted residues represent regions of homology of 8 or more amino acids between MAP1B and MAP1A.

FIG. 10 is a table showing clinical information for 95 patients.

DETAILED DESCRIPTION

Figure 1:
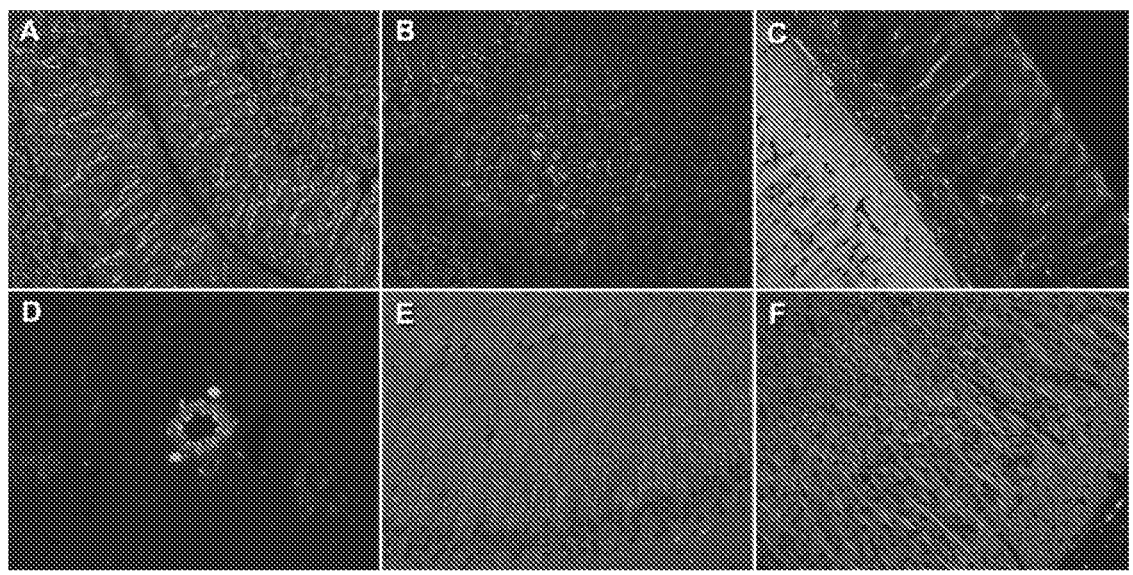
FIG. 1 is indirect immunofluorescence showing binding of patient's MAP1B (PCA-2) specific-IgG from serum (at 1:240 dilution) to a composite of mouse nervous system and other organ tissues. Panel A shows Purkinje cell cytoplasm and dendrites are brightly stained. Synaptic staining of the molecular layer (ML) and the granular layer (GL) are also seen. Panel B shows intense immunoreactivity in the cytoplasm of the cerebellar dentate neurons. Panel C shows ganglia within the myenteric plexus and nerve fibers within the smooth muscle of the stomach stain brightly. Nerves within the gastric mucosa are also stained. Panel D shows intense immunoreactivity of autonomic (sympathetic) nerves adjacent to a renal blood vessel. Panel E shows diffuse "synaptic" staining and staining of pyramidal cell cytoplasm and their dendrites in CA-1 region of the hippocampus. Panel F shows pyramidal cell' dendrites are stained in the cortex. The diffuse "synaptic" staining is also notable.

A specific IgG autoantibody marker (PCA-2) is found in serum of individuals presenting with paraneoplastic neurological disorders and/or cancers associated with PCA-2-specific autoantibodies (e.g., neuroendocrine tumors). The target of PCA-2 was identified herein as MAP1B, a microtubule-associated protein that is found throughout the central and peripheral nervous and is highly expressed in both developing neurons and in neuroendocrine tumors. PCA-2-specific autoantibodies may also be referred to as MAP1B-specific autoantibodies.

This document provides materials and methods for using MAP1B polypeptides or fragments thereof to detect PCA-2-specific autoantibodies in an individual that presents with a paraneoplastic neurological disorder and/or cancer associated with PCA-2-specific autoantibodies. The presence of PCA-2-specific autoantibodies can be used to diagnose the individual as having a paraneoplastic neurological disorder and/or cancer associate with PCA-2-specific autoantibodies. Also provided herein are materials and methods for treating an individual that presents with a paraneoplastic neurological disorder and/or cancer associated with PCA-2-specific autoantibodies. Any appropriate individual can be diagnosed or treated as described herein. Examples of individuals that can be subjected to the methods described herein include, without limitation, humans, non-human primates, monkeys, bovine species, pigs, horses, dogs, and cats.

Any appropriate paraneoplastic neurological disorders and/or cancer associated with PCA-2-specific autoantibodies can be diagnosed and/or treated using the methods and materials described herein. Paraneoplastic neurological disorders relate to autoimmune or inflammatory conditions that damage nervous system at any level from central nervous system to peripheral nervous system. In some cases, a paraneoplastic neurological disorder associated with PCA-2-specific autoantibodies can be a neurological disorder associated with a neuroendocrine tumor. Paraneoplastic neurological disorders associated with neuroendocrine tumors include, without limitation, encephalitis/encephalopathy, seizures, sleep disorders, cerebellar dysfunction/cerebellar degeneration/cerebellar ataxia, optic neuropathy, retinopathy, movement disorders/non voluntary movements, eye movement abnormalities, peripheral neuropathy, autonomic dysfunction, neuromuscular junction syndromes, Lambert-Eaton myasthenic syndrome (LEMS), Cushing syndrome, syndrome of inappropriate antidiuretic hormone secretion (SIADH), paraneoplastic cerebellar degeneration, encephalomyelitis, limbic encephalitis, brainstem encephalitis, opsoclonus myoclonus ataxia syndrome, and polymyositis. For example, an individual having LEMS can be diagnosed and/or treated using the methods and materials described herein. In some cases, a cancer associated with PCA-2-specific autoantibodies can be a neuroendocrine tumor. Neuroendocrine tumors can arise in many different areas of the body (e.g., lungs, intestine, pancreas, gastrointestinal tract, thymus, and thyroid). Examples of neuroendocrine tumors include, without limitation, SCLC, renal carcinoma, squamous cell skin carcinoma, extrapulmonary small-cell carcinoma (EPSCC), prostate adenocarcinoma, primary intrahepatic cholangiocarcinoma, Ewing sarcoma, nasopharyngeal carcinoma, lymphoma, large cell neuroendocrine carcinoma of the lung (LCNEC), gastroenteropancreatic neuroendocrine tumors (GEP-NET), pituitary tumors, thyroid tumors, and medullary carcinoma. For example, an individual having SCLC can be treated using the methods and materials described herein.

MAP1B Polypeptides and Anti-PCA-2 Antibodies

MAP1B polypeptides (and fragments thereof) can be used to detect PCA-2-specific autoantibodies. Examples of MAP1B polypeptide sequences (and the nucleic acids encoding such polypeptides) can be found in the National Center for Biotechnology Information (NCBI) GenBank. Examples of human of MAP1B polypeptide sequences include, without limitation, GenBank Accession Nos. AAA18904 (Version AAA18904.1; GI:473431), CAM06633 (Version CAM06633.1; GI:122703742), CAM12311 (Version CAM12311.1; GI:122703744), and P46821 (Version P46821.2; GI:317373388). Additional MAP1B sequences can be found, for example, in public databases. A representative human MAP1B sequence is shown in FIG. 8 (SEQ ID NO:1). In some cases, a fragment of MAP1B polypeptide can be used as described herein to detect PCA-2-specific autoantibodies. Examples of MAP1B fragments that can be used to detect a PCA-2-specific autoantibody can include, without limitation, fragments of SEQ ID NO:1 (e.g., amino acids 1-666 of SEQ ID NO:1, amino acids 576-1990 of SEQ ID NO:1, amino acids 1111-1690 of SEQ ID NO:1, amino acids 1611-2120 of SEQ ID NO:1, or amino acids 2040-2168 of SEQ ID NO:1).

A MAP1B polypeptide or fragment thereof can be provided in any appropriate context. In some cases, a MAP1B polypeptide or fragment thereof can be in a solution (e.g., a cell lysate). In some cases, a MAP1B polypeptide or fragment thereof can be in a solid substrate (e.g., a tissue such as brain (e.g., cerebellum, midbrain, cerebral cortex, or hippocampus), kidney, gut, stomach, or other tissues containing peripheral nerve elements).

In some cases, MAP1A polypeptides (and fragments thereof) can be used to detect PCA-2-specific autoantibodies. A representative human MAP1A sequence is shown in FIG. 9 (SEQ ID NO:2). Examples of MAP1A fragments that can be used to detect a PCA-2-specific autoantibody can include, without limitation, fragments of SEQ ID NO:2 (e.g., amino acids 1-670 of SEQ ID NO:2, amino acids 606-1204 of SEQ ID NO:2, amino acids 1181-1720 of SEQ ID NO:2, amino acids 1661-2200 of SEQ ID NO:2, or amino acids 2141-2803 of SEQ ID NO:2).

This document also provides nucleic acids and constructs encoding an MAP1B polypeptide (or fragment thereof) described herein. As used herein, nucleic acid (e.g., MAP1B nucleic acid) refers to RNA or DNA. As used herein with respect to nucleic acids, "isolated" refers to (i) a nucleic acid sequence encoding part or all of MAP1B polypeptide, but free of coding sequences that normally flank one or both sides of the nucleic acid sequences encoding MAP1B in the genome; or (ii) a nucleic acid incorporated into a vector or into the genomic DNA of an organism such that the resulting molecule is not identical to any naturally-occurring vector or genomic DNA.

A MAP1B polypeptide can have a sequence that deviates from a wild type MAP1B polypeptide sequence (e.g., SEQ ID NO:1), sometimes referred to as a variant sequence. For example, a MAP1B polypeptide sequence can have at least 80% sequence identity to SEQ ID NO:1. In some embodiments, an MAP1B polypeptide sequence can have at least 85% sequence identity, 90% sequence identity, 95% sequence identity, or at least 99% sequence identity to SEQ ID NO:1. Percent sequence identity is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in aligned sequences. The total number of aligned nucleotides or amino acids refers to the minimum number of MAP1B nucleotides or amino acids that are necessary to align the second sequence, and does not include alignment (e.g., forced alignment) with non-MAP1B sequences, such as those fused to MAP1B. The total number of aligned nucleotides or amino acids may correspond to the entire MAP1B sequence or may correspond to fragments of the full-length MAP1B sequence as defined herein.

Sequences can be aligned using the algorithm described by Altschul et al. (*Nucleic Acids Res.*, 25:3389-3402 (1997)) as incorporated into BLAST (basic local alignment search tool) programs, available at ncbi.nlm.nih.gov on the World Wide Web. BLAST searches or alignments can be performed to determine percent sequence identity between a MAP1B nucleic acid molecule and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a MAP1B sequence and another sequence, the default parameters of the respective programs are used.

MAP1B polypeptides may be obtained from human, mouse or other mammalian neuronal tissue, neuronal cell lines, or transfected cells (e.g., mammalian, *E. coli* or yeast) expressing a recombinant MAP1B nucleic acid, or the MAP1B polypeptide may be synthetic. Polypeptides can be purified. A "purified" polypeptide refers to a polypeptide that constitutes the major component in a mixture of components, e.g., 30% or more, 40% or more, 50% or more, 60% or more, 70% or more, 80% or more, 90% or more, 95% or more, or 99% or more by weight. Polypeptides may be purified by methods including affinity chromatography or immunosorbent affinity column.

Given a MAP1B polypeptide sequence (see, for example, SEQ ID NO:1), virtually any polypeptide fragment can be generated by, for example, proteolytic cleavage of a polypeptide or chemical synthesis. Fragments of a MAP1B polypeptide can contain one or more epitopic sites (e.g., B cell epitopes). Epitopic sites within MAP1B polypeptides that are pertinent to T-cell activation and suppression (e.g., MHC-I and MHC-II binding epitopes) can be determined by direct investigation, or by using computer algorithms. See, for example, Parker et al. (*J. Immunol.*, 152:163 (1994)) and Southwood et al. (*J. Immunol.*, 160:3363 (1998)).

This document also provides for an antibody, including a monoclonal antibody, with specific binding affinity for MAP1B polypeptides or antigenic fragments thereof. MAP1B polypeptides as described herein can be used to produce monoclonal or polyclonal anti-MAP1B antibodies having specific binding affinity for the MAP1B polypeptide. Such antibodies can be produced using techniques such as hybridoma technology and display technology. As used herein, anti-MAP1B antibodies having "specific binding affinity" for MAP1B polypeptides or fragments thereof are defined as those antibodies that preferentially bind MAP1B polypeptides or fragments thereof, but that do not bind or have very little affinity for non-MAP1B polypeptides. While the MAP1B-specific autoantibodies described herein are IgG antibodies, a recombinant "anti-MAP1B antibody" can be whole antibodies of any class (e.g., IgG IgA, IgM), portions or fragments of whole antibodies (e.g., Fab or (Fab)$_2$ fragments) having the desired specific binding affinity, an engineered single chain Fv molecule, or a chimeric molecule, e.g., an antibody that contains the binding specificity of one antibody (e.g., of murine origin) and the remaining portions of another antibody (e.g., of human origin).

This document also provides articles of manufacture (e.g., kits) containing one or more MAP1B polypeptides or fragments thereof. MAP1B polypeptides or fragments thereof that are included in an article of manufacture as described herein can be provided within a cell, in a solution in which they are soluble, or the MAP1B polypeptides or fragments thereof can be provided in a lyophilized form. The kit may further include a second substance that, for example, provides for a detectable signal. In addition, a kit can include directions for using the MAP1B polypeptides and/or directions for practicing a method described herein (i.e., detecting PCA-2-specific autoantibodies in a biological sample).

In some cases, a kit can be designed to include anti-MAP1B antibodies having binding affinity for MAP1B polypeptides or fragments thereof. The kit may also include MAP1B polypeptides or fragments thereof to be used as binding controls or to generate a standardized quantitative curve. The kit may further include a second substance that provides for detectable label. A kit typically includes directions for using an anti-MAP1B antibody (e.g., for detecting or purifying MAP1B polypeptides).

Methods of Detecting

This document also provides for methods of detecting PCA-2-specific autoantibodies. The presence of PCA-2-specific autoantibodies can be used to diagnose a paraneoplastic neurological disorder and/or a cancer associated with PCA-2-specific autoantibodies. In some cases, the detection of PCA-2 specific autoantibodies in patients with LEMS can predict the presence of SCLC. MAP1B polypeptides or fragments thereof can be used in various immunological techniques to detect a PCA-2-specific autoantibody. For example, MAP1B polypeptides can be used in an immunoassay to detect PCA-2-specific autoantibodies in a biological sample. MAP1B polypeptides used in an immunoassay can be in a cell lysate (e.g., a whole cell lysate or a cell fraction), or purified MAP1B polypeptides or fragments thereof can be used provided at least one antigenic site recognized by PCA-2-specific autoantibodies remains available for binding. Depending on the nature of the sample, either or both immunoassays and immunocytochemical staining techniques may be used. Enzyme-linked immunosorbent assays (ELISA), Western blot, and radioimmunoassays can be used as described herein to detect the presence of PCA-2-specific autoantibodies in a biological sample.

MAP1B polypeptides or fragments thereof may be used with or without modification for the detection of PCA-2-specific autoantibodies. Polypeptides can be labeled by either covalently or non-covalently combining the polypeptide with a second substance that provides for detectable signal. A wide variety of labels and conjugation techniques can be used. Some examples of labels that can be used include radioisotopes, enzymes, substrates, cofactors, inhibitors, fluorescers, chemiluminescers, magnetic particles, and the like.

A "biological sample," as used herein, is generally a sample from an individual. Non-limiting examples of biological samples include blood, serum, plasma, or cerebrospinal fluid. Additionally, solid tissues, for example, spinal cord or brain biopsies may be used.

Anti-MAP1B antibodies as described herein can be used in various immunological techniques for detecting MAP1B polypeptides. Depending on the nature of the sample, immunoassays (e.g., radioimmunoassays) and/or immunohistochemical/immunocytochemical staining techniques may be used. Liquid phase immunoassays (e.g., competitive inhibition radioimmunoassays) or solid phase immunoassays (e.g., antigen-capture or Western blot analysis) can also be used to detect MAP1B polypeptides. Additionally, enzyme-linked immunosorbent assays (ELISA) can be used for detecting the presence of MAP1B polypeptides.

Anti-MAP1B antibodies may be used with or without modification for the detection of MAP1B polypeptides. Anti-MAP1B antibodies can be labeled either directly or indirectly, and a wide variety of labels, including radioisotopes, enzymes, substrates, cofactors, inhibitors, fluorescers, chemiluminescers and magnetic particles. In some cases, an anti-MAP1B antibody having specific binding affinity for MAP1B polypeptides can be conjugated to an imaging agent. Suitable imaging agents include, but are not limited to, radioisotopes, such as $^{32}$P, $^{99}$Tc, $^{111}$In and $^{131}$I.

Methods of detecting MAP1B polypeptides and/or PCA-2-specific autoantibodies can include enumerating or isolating PCA-2-specific autoantibodies from an individual. This method may be used, for example, to monitor and/or evaluate an individual's immune response, disease state, and/or treatment response.

Methods of Treatment

This document also provides methods for treating an individual (e.g., a human) whose immune system is producing PCA-2-specific autoantibodies.

In some cases, MAP1B polypeptides can be used as described herein to diagnose a paraneoplastic neurological disorder and/or a cancer associated with PCA-2-specific autoantibodies in an individual, and an immunotherapy can be administered to the individual to treat the paraneoplastic neurological disorder and/or a cancer associated with PCA-2-specific autoantibodies. Examples of immunotherapies include, without limitation, immunomodulation (e.g., activation immunotherapies or suppression immunotherapies), antigen specific tolerance induction strategy (e.g., MAP1B specific tolerance induction strategy), and immunotherapy targeting MAP1B specific T cells and/or B cells. Examples of immunomodulatory agents that can be used to suppress the immune response include, without limitation, immunosuppressants (e.g., corticosteroids, mycophenolate mofetil, azathioprine, tacrolimus, cyclophosphamide, rituximab, and/or mTOR inhibitors). For example, a corticosteroid can be used to treat paraneoplastic neurological disorder and/or a cancer associated with PCA-2-specific autoantibodies. Examples of immunomodulatory agents that can be used to target T cells include, without limitation, cyclophosphamide and/or tacrolimus. For example, cyclophosphamide and/or tacrolimus can be used to treat paraneoplastic neurological disorder and/or a cancer associated with PCA-2-specific autoantibodies.

In some cases, MAP1B polypeptides described herein can be used in an apheresis method to treat a paraneoplastic neurological disorders and/or cancer associated with PCA-2-specific autoantibodies. For example, apheresis for the treatment of a paraneoplastic neurological disorders and/or cancer associated with PCA-2-specific autoantibodies can be used to remove PCA-2-specific autoantibodies from an individual. Methods and extracorporeal systems for apheresis (i.e., the process of withdrawing blood from an individual, removing components from the blood, and returning the blood, or blood depleted of one or more components, to the individual) can be used as described elsewhere (see, for example, U.S. Pat. Nos. 4,708,713; 5,258,503; 5,386,734; and 6,409,696). In some cases, an apheresis method can be used to remove PCA-2-specific autoantibodies from a body fluid of an individual. The method can include withdrawing a body fluid from an individual; removing a substantial portion of PCA-2-specific autoantibodies from the fluid; and returning the fluid to the individual. Antibodies removed can be of any class, e.g., IgG (such as IgG1, IgG2, IgG3, IgG4), IgM, IgD, IgA, or IgE antibodies.

As used herein, a "substantial portion" means removing at least 20% (e.g., at least: 20%; 30%; 40%; 50%; 60%; 65%; 70%; 75%; 80%; 85%; 90%; 93%; 95%; 96%; 97%; 98%; 99%; 99.5%; 99.8%; or even 100%) of the PCA-2-specific autoantibodies that were present in the body fluid prior to removal. The body fluid can be blood plasma or any other body fluid, e.g., lymph or cerebrospinal fluid. According to the methods described herein, depleting PCA-2-specific autoantibodies from individuals with a PCA-2-associated autoimmune disease may result in a reduction or a decrease in one or more of the symptoms.

Removal of PCA-2-specific autoantibodies is generally performed by contacting a body fluid with a MAP1B polypeptide or fragment thereof. The MAP1B polypeptide or fragment thereof can be bound to a solid support. Such solid supports can be, without limitation, membranes, fibers, spherical beads, or granules and can be made with a water-insoluble, preferably porous, biocompatible material, e.g., organic polymers such as agarose, dextran, and polyacrylamide, or inorganic porous materials such as porous glass or porous silica gel. Such materials are suitable or can be adapted (e.g., derivatized with appropriate chemical groups) for attachment of a MAP1B polypeptide.

When the body fluid is blood, the plasma and/or white blood cells can be separated from red blood cells (e.g., erythrocytes) and the red blood cells can be returned to the individual with or without white blood cells. Usually, the blood cells are returned to the individual with artificial rather than their original blood plasma. The "replacement fluid" (e.g., physiological saline) can be administered to the individual after removal of the fluid. Alternatively, the PCA-2-specific autoantibodies can be selectively removed from the blood plasma in the course of apheresis and the blood cells can be mixed with the PCA-2-specific autoantibody-depleted plasma and then re-infused as a mixture into the individual.

The system can be a continuous one in which, for example, blood is pumped out of a blood vessel (e.g., an artery or a vein) passed over a solid support derivatized with MAP1B polypeptides and pumped directly back into a blood vessel of the individual. As in non-continuous systems, blood cells can be separated from plasma prior to passing of the plasma over the solid support.

This document also provides methods of imaging MAP1B polypeptide-expressing cells in an individual. The method can include administering to the individual an effective amount of an anti-MAP1B antibody having specific binding affinity for a MAP1B polypeptide labeled with an imaging agent, for example, $^{32}$P, $^{99}$Tc, $^{111}$In or $^{131}$I, to bind to a MAP1B polypeptide released from, or accessible in, cells, and detecting any complex so formed. A suitable amount of an anti-MAP1B antibody is any amount that is effective to image cells, for example, labelled anti-MAP1B antibodies having about 0.1 mCi to about 50.0 mCi. In addition, an effective amount of an anti-MAP1B antibody may be an amount from about 0.01 mg to about 100 mg.

The invention will be further described in the following examples, which do not limit the scope of the invention described in the claims.

EXAMPLES

Example 1: Target and Antigen of PCA-2 in Paraneoplastic Neurological Disorders Associated with Small Cell Lung Cancer Purkinje cell antibody-type 2 (PCA-2) was described in 2000 as an IgG biomarker of paraneoplastic neurologic autoimmunity initiated by small-cell lung carcinoma (SCLC), with an ~280-kDa onconeural cytoplasmic antigen expressed in central and peripheral neural tissues and SCLC cells. PCA-2 screening was incorporated into Mayo Clinic's comprehensive serological evaluation for paraneoplastic neural autoantibodies. This example identified the autoantigen as a member of the microtubule-associated protein family (MAP1B), and further defined clinical, oncologic and immunohistochemical characteristics of PCA-2.

Patients

The Mayo Clinic Institutional Review Board approved tissue acquisition and review of patients' histories. Between January 1993 and May 30, 2016 the Mayo Clinic Neuroimmunology Laboratory tested approximately half a million serum or cerebrospinal fluid (CSF) specimens submitted for paraneoplastic neural autoantibody evaluation on a service basis. Of 118 patients with PCA-2 IgG documented immunohistochemically and by western blot, at least one archival frozen specimen was available for 96 (92 serum and 4 CSF) and clinical information was available for 95 patients, 22 through the Mayo Clinic medical record and 73 through communication with referring physicians. Control sera (98) included: 33 healthy subjects (Mayo Clinic Biobank), 17 patients with miscellaneous immunopathies (6 systemic lupus erythematosus [SLE], 6 Sjogren syndrome, 5 hypergammaglobulinemia), 15 patients with multiple sclerosis, and 32 patients with neurologic autoimmunity associated with an IgG autoantibody prominently reactive with cytoplasm of cerebellar purkinje cells (17 PCA-1 positive) (Greenlee et al., Ann Neurol 1983; 14:609-13), and both cytoplasm of cerebellar purkinje cells and their dendrites (16 Inositol Triphosphate Receptor (ITPR)-1 positive; Jarius et al., J Neuroinflammation 2014; 11:206).

Immunohistochemical Staining

Indirect immunofluorescence assay (IFA): Screening with patient serum and CSF and commercial monoclonal and polyclonal antibodies was performed on a cryosectioned composite of adult mouse tissues (4 μm): cerebellum, midbrain, cerebral cortex, hippocampus, kidney and gut. Sections were fixed using 4% paraformaldehyde, 1 min, permeabilized with 3-[(3-cholamidopropyl)dimethylammonio]-1-propanesulfonate (CHAPS) 0.5% in phosphate bufferd saline (PBS), 1 min, blocked 1 hour with normal goat serum (10% in PBS). After PBS-rinse, patient specimen was applied (serum pre-absorbed with bovine liver powder, 1:240 dilution; CSF non-absorbed, 1:2 dilution), or commercial IgG of the following specificities: MAP1A, rabbit polyclonal, Santa Cruz Biotechnology Inc. (Dallas, Tex., USA, MAP1B mouse monoclonal, BD Transduction Laboratories, San Jose, Calif., USA, MAP1B Rabbit polyclonal, (Protein Tech (Rosemont, Ill., USA). After 40 minutes and PBS wash, species-specific anti-IgG (conjugated with FITC or TRITC; Southern Biotechnology Associates, Inc, (Birmingham, Ala., USA) was applied and mounted cover slips using ProLong Gold anti-fade medium (containing DAPI; Molecular Probes ThermoFisher Scientific, USA). Fluorescent images were captured using Olympus BX51 Polarizing microscope with Olympus DP73 high-performance Peltier cooled, 17.28 megapixel camera. Patient specimens yielding positive results were titrated in doubling dilutions to determine the endpoint of autoantibody detection.

Dual Staining by Confocal Microscopy:

Colocalization studies utilized patient serum and commercial IgGs specific for MAP1A or MAP1B. Goat IgG secondary antibodies were TRITC or FITC conjugated and specific for rabbit or mouse IgG (Southern Biotechnology Associates, Inc, (Birmingham, Ala., USA), goat anti-human IgG was alexa fluor 594 conjugated (Molecular Probes ThermoFisher Scientific, USA). Confocal images were captured using Zeiss LSM780 microscope (63× or 40× water immersion lens).

Protein Purification and Sequencing

Antigen Preparation:

All steps were at 4° C. Adult mouse cerebellum and SCLC tumor xenografts (Lennon et al., The Journal of clinical investigation 2003; 111:907-13; Yu et al., Ann Neurol 2001; 49:146-54) were homogenized using a tissue homogeniser with buffer, 3 mL/g (10 mM Hepes pH 7.4, 1 mM $MgCl_2$, 1 mM EDTA and complete protease inhibitor cocktail [Rochea Indianapolis, Ind., USA]). Homogenate was clarified by centrifugation (150,000 g, 30 minutes), and supernate was stored at −80 C.

Antibody Purification:

Cerebellar proteins separated electrophoretically in 5% polyacrylamide gel (PAGE), then transferred electrophoretically to nitrocellulose membrane, and blocked in buffer (20 mM Tris, pH 7.6, 137 mM sodium chloride, 0.1% Tween-20) containing 10% powdered milk. Longitudinal edge strips were cut (0.5 cm) from the nitrocellulose and probed with patient IgG to locate the immunoreactive band (~280 kDa). The remaining non-exposed central region of the nitrocellulose, containing reactive band (9.5×0.8 cm), at approximately 280 kDa was cut horizontally (and also a control strip from a non-reactive region). Patient serum (diluted 1:500) was applied to the cut nitrocellulose strips, 1 hour and, after extensive washing, bound human IgG was eluted in 100 mM acetic acid, neutralized, dialyzed against PBS and concentrated. To confirm PCA-2 specificity, the eluted IgG was tested by IFA on mouse tissue sections.

Protein Purification and Sequencing:

Patient's affinity purified IgG was complexed to Protein G magnetic beads (Dynabeads, Invitrogen ThermoFisher Scientific, USA). After washing, cerebellar protein extract was added (1 hour), washing was repeated, and beads were boiled 5 minutes in 2× sample buffer. Eluted sample was electrophoresed in 5% (PAGE) and proteins were located by Coomassie G-250 (Bio-Rad, Hercules, Calif., USA) staining and by western blot. The immunoreactive band was cut from the stained gel, reduced, alkylated with iodoacetamide, and digested with trypsin. Peptides in the digested sample were analyzed using nano high-pressure liquid chromatography electrospray tandem mass spectrometry (nano-LC-ESI-MS/MS).

Constructs:

cDNA encoding full length MAP1A and MAP1B proteins (Genecopoeia Clone # HOC23132 and HOC23292) were used as template for amplification reactions using either Pfx (Invitrogen) or AmpliTaq (Applied Biosytems) DNA polymerase. The coding regions of both genes were amplified as five individual fragments (Table 1) and cloned into pET102D bacterial expression vector (Invitrogen). Clones were selected and sequence integrity was verified by Sanger sequencing. BL-21 cells (Invitrogen) were transformed with plasmid DNA, grown under antibiotic selection and, at optical density of 0.5-0.8, were induced with IPTG (400 mM). After 2.5 additional hours at 37° C., cells were pelleted and protein expression was verified by extraction (50 mM NaPO4, 400 mM NaCl, 100 mM KCl, 10% glycerol, 0.5% Triton X-100, 10 mM Imidizole), and western blot (horse radish peroxidase conjugated V5 epitope tag-specific IgG [Invitrogen]).

Absorption of Patients' Serum with MAP1B

Following incubation with bovine liver powder, 50 µL of serum from 2 MAP1B (PCA-2) IgG-positive patients (patient 74, 82, table 2) and 1 positive ANNA-1(anti-Hu) patient, were incubated with 10 µL of recombinant MAP1B protein, fragment 1, overnight. Postincubation serum was tested by IFA on mouse tissue sections.

Results

Characterization of the Autoantibody

Immunohistochemical Distribution of the Neural Antigen:

The initial report of the PCA-2 antigen's immunohistochemical distribution noted striking cytoplasmic staining of cerebellar purkinje neuronal perikaryon and dendrites (FIG. 1a), dentate neurons (FIG. 1b), myenteric ganglia and enteric nerves extending into gastric mucosa (FIG. 1c) and sympathetic nerves innervating kidney (FIG. 1d). Examination of additional CNS regions represented in the extended mouse tissue substrate revealed a diffuse glow over synapse-rich regions of cerebral cortex and hippocampus (FIG. 1e,f) and staining of dendrites of hippocampal pyramidal neurons (mostly CA-1) and cerebral cortex (FIG. 1e, 1f).

Immunochemical Characterization of the Autoantigen

Figure 2A:
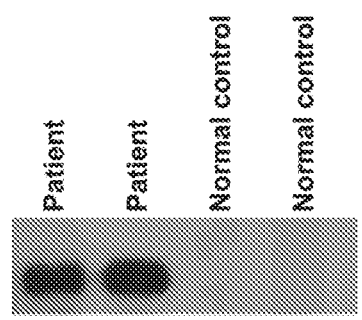
FIGS. 2A-2B show that PCA-2 IgG binds to a native neural protein. A) A common band (~280 kDa by reference to molecular weight standards) was revealed by IgG (PCA-2) in patients' sera (lanes 1 and 2), but not by IgG in control human serum (lanes 3 and 4). To verify specificity, patient IgG was affinity purified on the putative antigenic band and a control band. B) Eluates from the putative antigenic band and control band were reapplied to the composite mouse tissue substrate slide, and compared to the original immunostaining pattern of whole patient serum IgG on the composite mouse tissue slides. The eluate from the putative antigenic band revealed an identical pattern of staining as shown in FIG. 1. Panel A shows Purkinje cells' and their dendrites are brightly stained on a background of diffuse "synaptic" staining of the molecular layer (ML) and the granular layer (GL) and Panel B shows Ganglia within the myenteric plexus and nerve fibers within the smooth muscle of the stomach stain brightly.
Figure 2B:
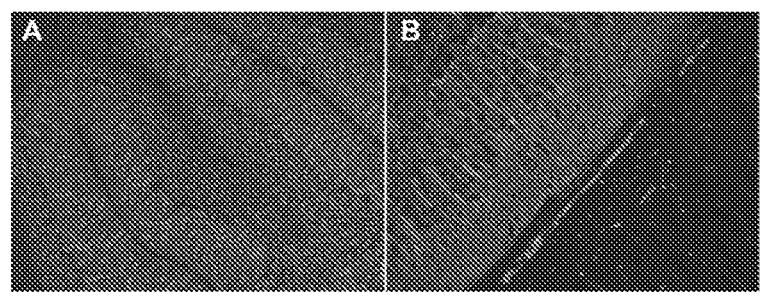

PCA-2 IgG Binds to a ~280 kDa Native Neural Protein:

Western blot probing of mouse brain proteins with patient IgGs confirmed a common immunoreactive band, ~280 kDa; control human IgGs were non-reactive (FIG. 2A). IgG eluted from the immunoreactive region of nitrocellulose, but not from a control region, replicated the original patient serum IgG immunostaining pattern when applied to mouse tissue sections (FIG. 2B; compare FIG. 1). Mass spectrometry analysis of proteins captured by the eluted IgG when immobilized on magnetic beads identified three candidate proteins of ~280 kDa mass: MAP1B (270 kDa), MAP1A (326 kDa), and MAP2 (199 kDa) (Sato-Yoshitake et al., *Neuron* 1989; 3:229-38; Lim et al., *J Biol Chem* 2000; 275(27): 20578-87).

Confocal Microscopy Supports MAP1B as Primary Antigenic Target.

Figure 3A:
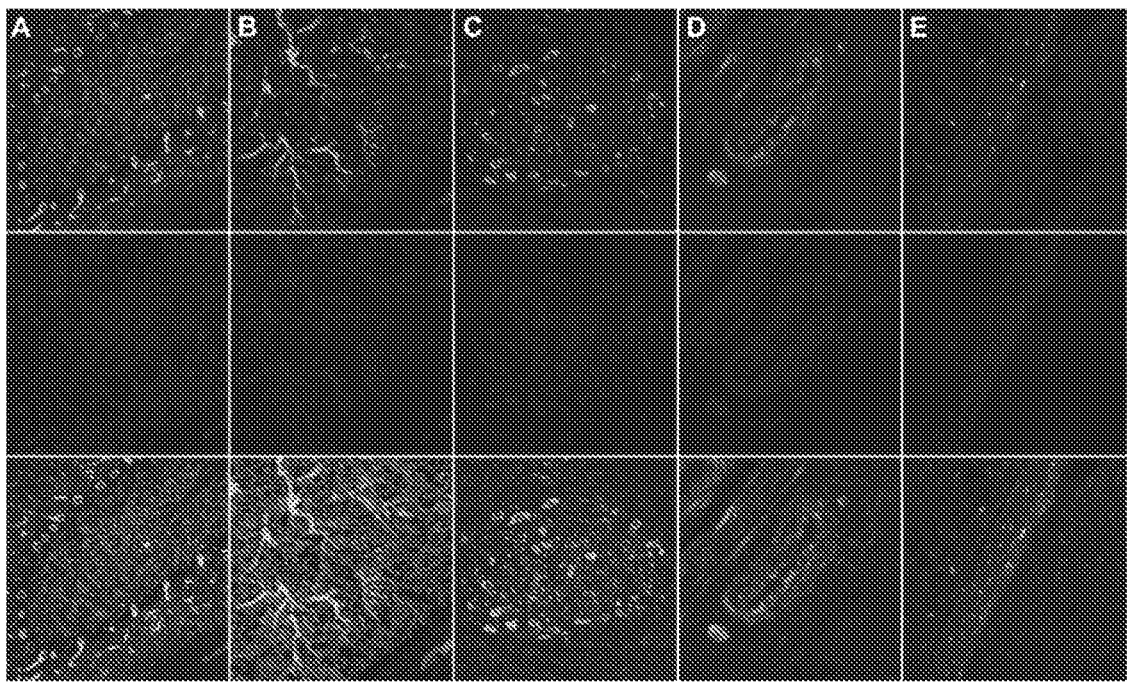
FIGS. 3A-3B show that patient IgG colocalizes with MAP1B immunoreactivity in mouse brain. Colocalization with MAP1A is also observed in some but not all regions. A) Top row: commercially available MAP1B autoantibodies; middle row: patient IgG; and bottom row, merged images. Column A shows cerebellar Purkinje cells and dendrites, Column B shows dendrites in higher magnification, Column C shows neuronal cells in dentate nucleus of cerebellum, Column D shows autonomic (sympathetic) nerves adjacent to renal arterial vessels, and Column E shows myenteric plexus with nerve fibers in the stomach smooth muscle. B) Top row: commercially available MAP1A autoantibodies; middle row: patient IgG; and bottom row, merged images. Panel A shows myenteric plexus where colocalization not observed; some staining is observed but not as intense and diffused. Panel B shows dentate neuronal cells are not stained. Panel C shows staining within gastric mucosa. Panels D and E shows colocalization observed in cerebellar Purkinje cells and dendrites, respectively.
Figure 3B:
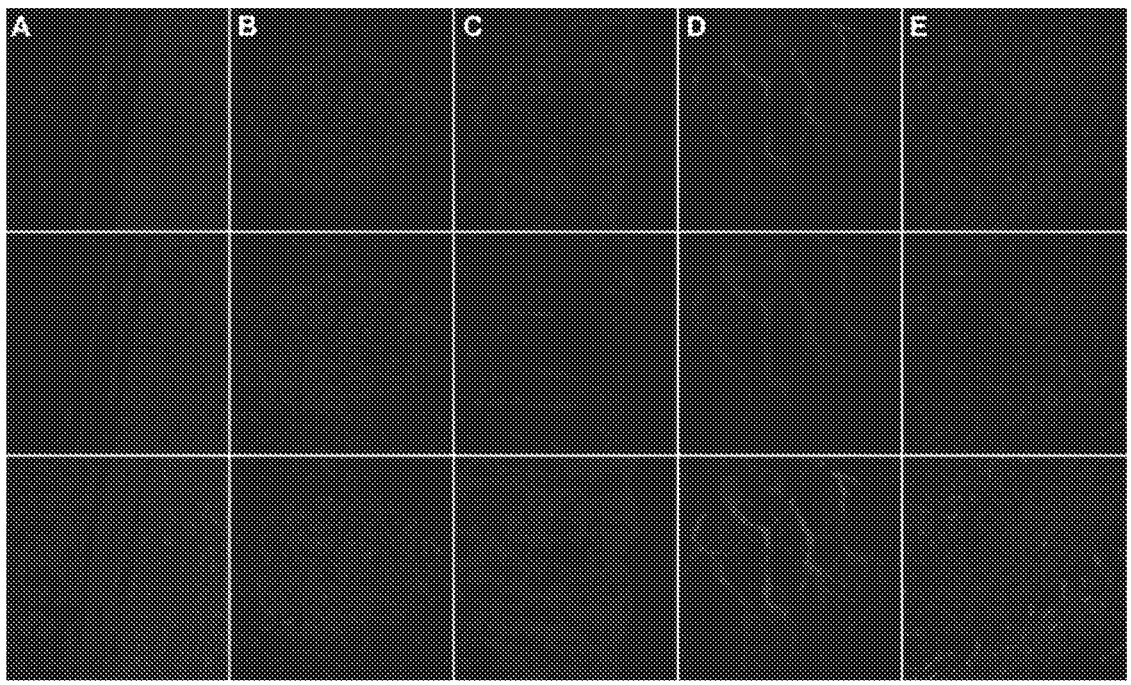

Commercial IgG specific for MAP1B yielded a staining pattern on mouse tissues identical to that of patient IgG (FIG. 3A). MAP1A-specific IgG yielded a similar pattern in some but not all nervous system regions (FIG. 3B). The staining pattern yielded by MAP2 IgG did not resemble that of patient IgG (not shown).

Figure 4:
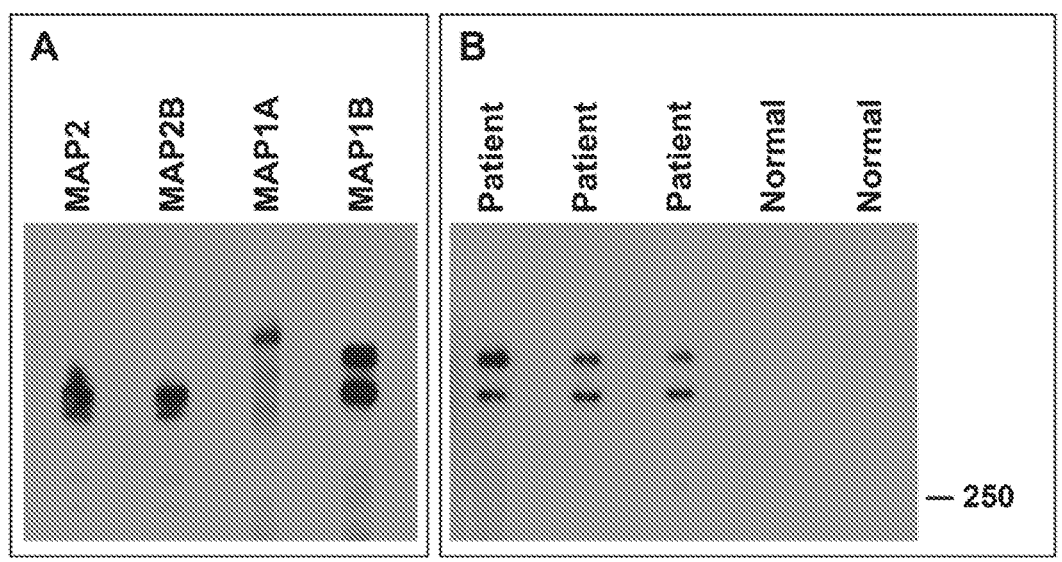
FIGS. 4A-4B show that MAP1B antibodies (A) and patients' IgG (B) bind to proteins of similar molecular weight in western blot. Western blot of mouse brain proteins reveals binding of commercially available MAP1B antibodies and patient IgG to bands with similar molecular weights and staining pattern. The commercially available antibodies to MAP1A, MAP2 and MAP2B bind to proteins of different molecular weights. Section A was taken at a lower exposure to reduce extent of signal and allow comparison with patient signal in section B. Normal controls show no band.

Western Blot Characterization of the Antigen:

Western blot analysis revealed that recombinant MAP1B had the same electrophoretic mobility as the native protein identified by patient IgG (FIG. 4); MAP1A and MAP 2 both differed, as predicted from their known properties (Sato-Yoshitake et al., *Neuron* 1989; 3:229-38).

Fragment 1 of MAP1B (Encompassing Residues 1-666) Contains the Principal Antigenic Region(s) Recognized by PCA-2:

Coding regions of both MAP1B and MAP1A genes were amplified as five individual fragments (Table 1) that overlapped by approximately 60-70 residues (FIG. 8). Serum (diluted 1:500) or CSF (diluted 1:50) from 40 PCA-2 IgG-positive patients were tested by western blot for polypeptide-reactive IgG on all 10 fragments (MAP1A #1-5, MAP1B #1-5). IgG in 40 of 40 specimens bound to MAP1B #1 (FIG. 5); additional IgGs in a minority of patients bound to other MAP fragments (FIG. 5). IgG in 55 of the remaining 57 PCA-2 IgG positive sera bound to MAP1B fragment 1 by western blot.

TABLE 1 cDNAs encoding full length MAP1A and MAP1B proteins served as template for PCR amplification reactions. The coding regions for each gene were amplified as five individual fragments and cloned into bacterial expression vectors.

|  | Fragment number | Amino acids encompassed | Number of amino acids in fragment | number of residues overlapping the previous fragment |
|---|---|---|---|---|
| MAP1A | 1 | 1-670 | 670 | N/A |
|  | 2 | 606-1240 | 635 | 65 |
|  | 3 | 1181-1720 | 540 | 60 |
|  | 4 | 1661-2200 | 540 | 60 |
|  | 5 | 2141-2803 | 663 | 60 |
| MAP1B | 1 | 1-666 | 666 | N/A |
|  | 2 | 576-1190 | 615 | 91 |
|  | 3 | 1111-1690 | 580 | 80 |
|  | 4 | 1611-2120 | 510 | 80 |
|  | 5 | 2040-2468 | 428 | 80 |

Microtubule-associated protein 1A and 1B [*Homo sapiens*]

Figure 6:
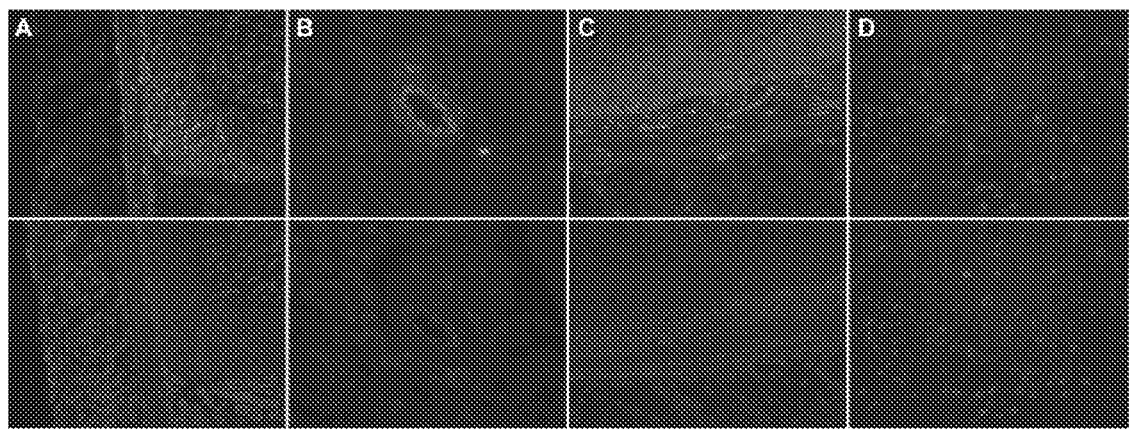
FIG. 6 shows elimination of patient IgG by MAP1B fragment 1 antigen. The characteristic staining pattern of patient IgG (pre absorption, top row) is eliminated after incubation of patient sera with recombinant MAP1B (post absorption, bottom row). Panel A shows cerebellar Purkinje cells and dendrites. Panel B shows autonomic (sympathetic) nerves adjacent to renal arterial vessels. Panel C shows myenteric plexus with nerve fibers in the stomach smooth muscle. Panel D shows neuronal cells in dentate nucleus of cerebellum from an ANNA-1 positive patient with no loss of staining after absorption with MAP1B fragment 1.

Recombinant MAP1B Protein Abrogates Tissue Binding by Patient IgG:

Preincubation of serum of two PCA-2 positive patients with MAP1B fragment 1, abolished the PCA-2 IgG staining pattern (FIG. 6A-C). This preincubation did not diminish the immunostaining intensity of ANNA-1 (anti-Hu) IgG in serum of a control patient with SCLC-related paraneoplastic neurologic autoimmunity (FIG. 6D).

Diverse Neurologic Accompaniments of MAP1B Autoimmunity

Clinical information was available for 95 patients (table 3, FIG. 10). The median age at neurologic symptom onset was 68 years (22-89); 55 patients (47%) were women and 82% (55/67) had history of tobacco use. Neurologic presentations varied and in the majority of cases symptoms and signs were subacute in onset (61%).

TABLE 2

Predominant Neurological Manifestations, MRI Findings and Coexisting Neural Antibodies in MAP1B-IgG (PCA-2) positive patients.

| Level involved | Number of patients (%) (data available in 95 patients) | Neurological Manifestations |
|---|---|---|
| Cerebral cortex | 30 (30%) | Encephalopathy/cognitive decline (26), Limbic encephalitis (7), Scondary generalized seizures (3), complex partial seizures (7), lethargy (5), hallucinations (3), |

TABLE 2-continued

Predominant Neurological Manifestations, MRI Findings and Coexisting Neural Antibodies in MAP1B-IgG (PCA-2) positive patients.

| | | |
|---|---|---|
| | | personality changes (3), paranoia (2), |
| Diencephalon | 6 (6%) | Sleep disturbance: Insomnia (5), hypersomnia (1) |
| Cerebellum | 36 (38%)) | Ataxia only (30) |
| Optic nerve/retina | 8 (8%) | optic neuropathy (4, 2 with ON enhancement on MRI) - 3 with CRMP5-IgG, retinal involvement (5) - 2 with CRMP5-IgG involvement |
| Brainstem/ Basal ganglia | | 5 Parkinsonism/dystonia/chorea (all 3 patients with chorea had CRMP-5 IgG, 1 of 2 patients with dystonia had amphiphysin IgG), 7 diplopia and eye movement abnormality (7, 3 with CRMP-5 and 1 with ANNA-1), nausea and vomiting (1) |
| Peripheral Nerve | 50 (53%) 43 (45%) | Paresthesia (22), pain/burning/ dysesthesia (9), muscle weakness (13) |
| Somatic Autonomic | 14 (15%) | Orthostatis (2), GI motility disorder (8), |
| Neuromuscular Junction | 5 (5%) | Lambert Eaton syndrome |
| Multifocal presentations | 45 (47%) | |
| Temporal lobe involvement | 2 (5) | ANNA-1 (2), CRMP-5 (1) | Limbic encephalitis (2) |
| Caudate nucleus atrophy | 1 (2) | | Involuntary movements |
| Brachial plexus | 1 (2) | | Brachial plexities (bilateral) |

Frequency of Co-existing Neural Autoantibodies (specimen available in 118 patients)

| Antibody specificity | Number (%) of patients | Ab | N (%) of patients |
|---|---|---|---|
| CRMP5 | 30 (25%) | ANNA-1 | 15 (13%) |
| VGCC P/Q type | 24 (20%) | GAD 65 | 18 (15%) |
| VGKC complex* | 8 (7%) | Alpha 3 | 7 (6%) |
| ARBi | 4 (3%) | GABA-B | 3 (3%) |
| Amphphysin | 2 (2%) | VGCC N type | 2 (2%) |
| AMPA | 2 (2%) | AGNA-1 (Sox-1) | 2 (2%) |
| >1 coexisting | 10 (8%) | | |

MRI findings (MRI scans available in 44 patients)

| Finding | Number of patients (%) | Coexisting neural autoantibody | Neurologic manifestation |
|---|---|---|---|
| Normal Mri | 15 (35) | | |
| Nonspecific changes | 8 (18) | | |
| Spinal involvement | 5 (11) | ANNA-1 (1) | Sensory neuropathy (2), cerebellar (2), limbic encephalitis (1), myelopathy (2) |
| Brain atrophy | 4 (9) | CRMP-5 (2), ANNA-1 (1) | Cerebellar (4), neuropathy (1), limbic encephalitis (1) |
| Cerebellar atrophy | 3 (7) | ANNA-1 (1), CRMP-5 (1) | Cerebellar (3) |
| Diffuse white matter leisions | 3 (7) | | Myelopathy (1), Cerebellar (1) |
| Optic nerve involvement | 2 (5) | CRMP-5 (1) | Optic neuropathy/ neuritis |
| Meningial enhancement | 2 (5) | | Encephalopathy (1), Cerebellar (1), Neuropathy (1) |

*None of the 96 available sera were positive for anti-Leucine-Rich, Glioma Inactivated 1 (LGI1) or contactin-associated protein-like 2 (CASPR2) antibodies.

Peripheral neuropathy, the most common presentation, was reported in 50 patients (53%); 44 had sensory-motor neuropathy (confirmed by EMG in 16), 14 had dysautonomia and other levels of the nervous system were affected in 34 patients. Cerebellar dysfunction was reported in 36 patients (38%). Cortical/subcortical involvement also was commonly encountered; encephalopathy/cognitive decline was reported in 26 patients (27%) of whom 5 had seizures.

Ten patients had symptoms referable to the anterior visual system: The following findings were documented in the medical/laboratory record: disc edema in 3, optic nerve involvement in 4 (3 with CRMP-5 IgG), enhancement of optic nerves on MRI in 2 (1 with CRMP-5 IgG), retinopathy in 5 (3 with CRMP-5 IgG).

Coexisting neural antibodies were detected in 79 of 118 (67%) patients (table 2). The two most common were CRMP5-IgG (25%) and voltage gated calcium channel antibodies (22%).

Reports of MRI brain were available for review in 44 patients: 15 (35%) were normal, 8 (18%) had nonspecific white matter changes in the brain and 20 patients (45%) had substantial changes on MM (table 2). The most common disease relevant findings were spinal cord involvement (5 with T2 hyper-intensities, 3 with enhancement), cerebral atrophy (4), optic nerve involvement (2, 1 with enhancement) and temporal lobe involvement (2).

MAP1B-IgG alone was detected in 4/5 patients with spinal cord involvement, 2/2 patients with meningeal enhancement and 1/2 patients with optic nerve involvement (the other patient had co-existing CRMP-5 IgG). More than half of the patients with cerebellar or cerebral atrophy and temporal involvement had additional antibodies including CRMP5-IgG and ANNA-1.

Results of CSF examination were available for 29 patients: 15 (52%) had pleomorphic leukocytosis (median white cell count, 20, range 6-162, normal reference range ≤5 per high power field); 21 (74%) had elevated protein (median 60 mg/dL, range 37-203, normal ≤35 mg/dL).

Oncologic Associations of MAP1B-IgG (PCA-2)

Among 84 patients with adequate oncologic evaluation information, cancer was found in 66 (79%; table 3). The detection frequency was higher in 44 patients who were singularly seropositive (89%). Lung cancer was most common (80% of all cancers). Small-cell carcinoma was 3 times more common than non-small-cell lung carcinoma (46% and 17%, P<0.01). Cancer diagnosis followed the neurologic presentation in 55% of cases. The median survival for 14 of 39 patients who had SCLC and adequate follow up information was 54 months (range 3-164).

TABLE 3

Numbers (% frequency) and types of cancer detected in PCA-2
IgG-positive patients with adequate oncologic evaluation.

| Cancer type (n/%) | PCA-2 IgG with or without other neural autoantibody) n = 85 | PCA-2 IgG only n = 45 | Cancer diagnosis followed neurologic presentation n (%) | Survival, number of patients†; months; median (range) | |
|---|---|---|---|---|---|
| | | | | Alive at last follow-up | Deceased at last follow-up |
| All malignancies | 67 (79%)** | 40 (88.8%) | 36 (53.7%) | 6; 43 (2.5-86) | 16; 20.5 (3-164) |
| Lung  SCLC | 39 (46%) | 18 (40%) | 26 (38.8%) | 3; 84 (60-86) | 11; 22 (3-164) |
|  NSCLC | 14 (16%) | 11 (24.4%) | 6 (9%) | 1; 4 | 4; 15 (3-42) |
| Breast | 5 (6%)*** | 3 (6.7%) | 0 | NA | NA |
| Other malignancy* | 9 (11%) | 8 (17.8%) | 3 (4.5%) | N = 2, 14.25 (2.5-26) | n = 1, 23 |

Figure 7:
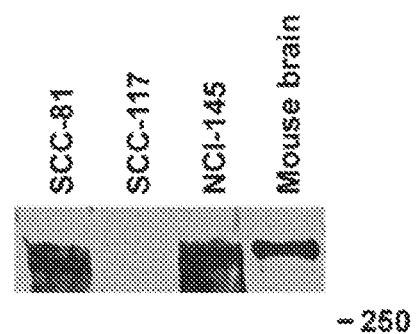
FIG. 7 shows that SCLC tumors express MAP1B. Lanes 1-3 are small cell lung tumors screened with MAP1B commercial antibody. Lane 1, Mayo Clinic Small Cell Cancer Cell line (SCC)-81, positive; lane 2, SCC-117 negative; Lane 3, National cancer institute-146 (SCLC cell line) positive. Lane 4 is a mouse brain screened with MAP1B as positive control. Neurological diagnosis of the small cell carcinoma patients from whom the tumors were resected from: SCC 2, 4, 17, 18, 24 (not shown)—Lamber eaton myasthenic syndrome (LEMS), SCC-21, 59 (not shown)—no neurologic symptoms, SCC 81—sensory motor peripheral neuropathy, Scc 117—ataxia and sensory neuropathy, NCI-146—information not available.

*renal carcinoma (1), squamous cell skin carcinoma (1), extrapulmonary small-cell carcinoma - pancreas (1), prostate adenocarcinoma (2), primary intrahepatic cholangiocarcinoma (1), Ewing sarcoma (1), nasopharyngeal carcinoma (1), lymphoma (1).
**65 proven histologically, 2 PET/imaging based
***all women
†Long term follow-up data regarding survival available for only 22 patients
NA = no data available Western blot analysis of proteins extracted from 10 SCLC tumor cell lines with commercial MAP1B-specific IgG confirmed MAP1B protein expression in 6 (FIG. 7).

Data regarding response to immunotherapy were available for only 26 patients: 14 had physician reported benefit from immunosuppression (neurologic symptoms stabilized or improved); 8/16 had a beneficial response to corticosteroids, 3/4 to plasmapheresis, 2/2 to cyclophosphamide and 0/2 to high dose IV immune globulin. Some neurologic benefit was reported in 11 of 15 patients after chemotherapy for cancer.

These results demonstrated that MAP1B, the PCA-2 autoantigen, represents a novel target in paraneoplastic neurologic disorders with a high predictive value for SCLC. Its relatively high prevalence, compared with other recognized paraneoplastic neural autoantibodies, justifies its testing in comprehensive paraneoplastic neural autoantibody evaluation.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of detecting the presence or absence of a Purkinje cell antibody-type 2 (PCA-2)-specific autoantibody in a biological sample from an individual, comprising the steps of:
contacting said biological sample with a microtubule associated protein 1B (MAP1B) polypeptide, or fragment thereof comprising amino acid residues 1-666, 540-693, 576-1190, 1111-1690, 1611-2120, or 2040-2468 of SEQ ID NO:1, to form a MAP1B-PCA-2-specific autoantibody complex if said biological sample contains said PCA-2-specific autoantibody; and
detecting the presence or absence of said complex.

2. The method of claim 1, wherein said method comprises performing a Western blot to detect said complex.

3. The method of claim 1, wherein said method comprises detecting the presence of said complex.

4. The method of claim 1, wherein said method comprises detecting the absence of said complex.

5. The method of claim 1, wherein said biological sample is selected from the group consisting of serum, plasma, cerebrospinal fluid, and blood.

6. A kit comprising (a) a MAP1B polypeptides consisting of amino acid residues 1-666, 540-693, 576-1190, 111-1690, 1611-2120, or 2040-2468 of SEQ ID NO:1, covalently or non-covalently attached to a label and (b) an anti-MAP1B antibody covalently or non-covalently attached to a label.

7. The kit of claim 6, wherein said kit comprises said anti-MAP1B antibody.

8. The kit of claim 7, wherein said anti-MAP1B antibody is a monoclonal antibody having specific binding affinity for said MAP1B polypeptide or said fragment thereof.

9. The kit of claim 6, further comprising a PCA-2-specific autoantibody.

10. A method of treating an individual having a paraneoplastic neurological disorder associated with PCA-2-specific autoantibodies, said method comprising:
    identifying an individual as having a paraneoplastic neurological disorder associated with PCA-2-specific autoantibodies by a method comprising:
    (i) contacting a biological sample from said individual with a MAP1B polypeptide, or fragment thereof comprising amino acid residues 1-666, 540-693, 576-1190, 1111-1690, 1611-2120, or 2040-2468 of SEQ ID NO:1, to form a MAP1B-PCA-2-specific autoantibody complex if said biological sample contains said PCA-2-specific autoantibody, and
    (ii) detecting the presence of said complex; and
    administering an immunomodulatory agent to said individual.

11. The method of claim 10, wherein said immunomodulatory agent comprises a corticosteroid.

12. The method of claim 10, wherein said immunomodulatory agent comprises cyclophosphamide.

13. The method of claim 10, wherein said immunomodulatory agent comprises tacrolimus.

14. A method of treating a paraneoplastic neurological disorder associated with PCA-2-specific autoantibodies, wherein said method comprises administering an immunomodulatory agent to an individual identified as having said disorder associated with PCA-2-specific autoantibodies by a method comprising:
    (a) contacting a biological sample from said individual with a MAP1B polypeptide, or fragment thereof comprising amino acid residues 1-666, 540-693, 576-1190, 1111-1690, 1611-2120, or 2040-2468 of SEQ ID NO:1, to form a MAP1B-PCA-2-specific autoantibody complex if said biological sample contains said PCA-2-specific autoantibody, and
    (b) detecting the presence of said complex.

15. The method of claim 14, wherein said immunomodulatory agent comprises a corticosteroid.

* * * * *

SEQUENCE LISTING

```
<160> NUMBER OF SEQ ID NOS: 2

<210> SEQ ID NO 1
<211> LENGTH: 2468
<212> TYPE: PRT
<213> ORGANISM: Homo sapiens

<400> SEQUENCE: 1

Met Ala Thr Val Val Val Glu Ala Thr Glu Pro Glu Pro Ser Gly Ser
1               5                   10                  15

Ile Ala Asn Pro Ala Ala Ser Thr Ser Pro Ser Leu Ser His Arg Phe
            20                  25                  30

Leu Asp Ser Lys Phe Tyr Leu Leu Val Val Gly Glu Ile Val Thr
        35                  40                  45

Glu Glu His Leu Arg Arg Ala Ile Gly Asn Ile Glu Leu Gly Ile Arg
    50                  55                  60

Ser Trp Asp Thr Asn Leu Ile Glu Cys Asn Leu Asp Gln Glu Leu Lys
65                  70                  75                  80

Leu Phe Val Ser Arg His Ser Ala Arg Phe Ser Pro Glu Val Pro Gly
                85                  90                  95

Gln Lys Ile Leu His His Arg Ser Asp Val Leu Glu Thr Val Val Leu
            100                 105                 110

Ile Asn Pro Ser Asp Glu Ala Val Ser Thr Glu Val Arg Leu Met Ile
```

-continued

```
            115                 120                 125
Thr Asp Ala Ala Arg His Lys Leu Leu Val Leu Thr Gly Gln Cys Phe
            130                 135                 140
Glu Asn Thr Gly Glu Leu Ile Leu Gln Ser Gly Ser Phe Ser Phe Gln
145                 150                 155                 160
Asn Phe Ile Glu Ile Phe Thr Asp Gln Glu Ile Gly Glu Leu Leu Ser
                165                 170                 175
Thr Thr His Pro Ala Asn Lys Ala Ser Leu Thr Leu Phe Cys Pro Glu
            180                 185                 190
Glu Gly Asp Trp Lys Asn Ser Asn Leu Asp Arg His Asn Leu Gln Asp
            195                 200                 205
Phe Ile Asn Ile Lys Leu Asn Ser Ala Ser Ile Leu Pro Glu Met Glu
            210                 215                 220
Gly Leu Ser Glu Phe Thr Glu Tyr Leu Ser Glu Ser Val Glu Val Pro
225                 230                 235                 240
Ser Pro Phe Asp Ile Leu Glu Pro Pro Thr Ser Gly Gly Phe Leu Lys
                245                 250                 255
Leu Ser Lys Pro Cys Cys Tyr Ile Phe Pro Gly Gly Arg Gly Asp Ser
            260                 265                 270
Ala Leu Phe Ala Val Asn Gly Phe Asn Met Leu Ile Asn Gly Gly Ser
            275                 280                 285
Glu Arg Lys Ser Cys Phe Trp Lys Leu Ile Arg His Leu Asp Arg Val
            290                 295                 300
Asp Ser Ile Leu Leu Thr His Ile Gly Asp Asp Asn Leu Pro Gly Ile
305                 310                 315                 320
Asn Ser Met Leu Gln Arg Lys Ile Ala Glu Leu Glu Glu Glu Gln Ser
                325                 330                 335
Gln Gly Ser Thr Thr Asn Ser Asp Trp Met Lys Asn Leu Ile Ser Pro
            340                 345                 350
Asp Leu Gly Val Val Phe Leu Asn Val Pro Glu Asn Leu Lys Asn Pro
            355                 360                 365
Glu Pro Asn Ile Lys Met Lys Arg Ser Ile Glu Glu Ala Cys Phe Thr
            370                 375                 380
Leu Gln Tyr Leu Asn Lys Leu Ser Met Lys Pro Glu Pro Leu Phe Arg
385                 390                 395                 400
Ser Val Gly Asn Thr Ile Asp Pro Val Ile Leu Phe Gln Lys Met Gly
                405                 410                 415
Val Gly Lys Leu Glu Met Tyr Val Leu Asn Pro Val Lys Ser Ser Lys
            420                 425                 430
Glu Met Gln Tyr Phe Met Gln Gln Trp Thr Gly Thr Asn Lys Asp Lys
            435                 440                 445
Ala Glu Phe Ile Leu Pro Asn Gly Gln Glu Val Asp Leu Pro Ile Ser
            450                 455                 460
Tyr Leu Thr Ser Val Ser Ser Leu Ile Val Trp His Pro Ala Asn Pro
465                 470                 475                 480
Ala Glu Lys Ile Ile Arg Val Leu Phe Pro Gly Asn Ser Thr Gln Tyr
                485                 490                 495
Asn Ile Leu Glu Gly Leu Glu Lys Leu Lys His Leu Asp Phe Leu Lys
            500                 505                 510
Gln Pro Leu Ala Thr Gln Lys Asp Leu Thr Gly Gln Val Pro Thr Pro
            515                 520                 525
Val Val Lys Gln Thr Lys Leu Lys Gln Arg Ala Asp Ser Arg Glu Ser
            530                 535                 540
```

```
Leu Lys Pro Ala Ala Lys Pro Leu Pro Ser Lys Ser Val Arg Lys Glu
545                 550                 555                 560

Ser Lys Glu Glu Thr Pro Glu Val Thr Lys Val Asn His Val Glu Lys
                565                 570                 575

Pro Pro Lys Val Glu Ser Lys Glu Lys Val Met Val Lys Lys Asp Lys
            580                 585                 590

Pro Ile Lys Thr Glu Thr Lys Pro Ser Val Thr Glu Lys Glu Val Pro
        595                 600                 605

Ser Lys Glu Glu Pro Ser Pro Val Lys Ala Glu Val Ala Glu Lys Gln
    610                 615                 620

Ala Thr Asp Val Lys Pro Lys Ala Lys Glu Lys Thr Val Lys Lys
625                 630                 635                 640

Glu Thr Lys Val Lys Pro Glu Asp Lys Lys Glu Glu Lys Glu Lys Pro
                645                 650                 655

Lys Lys Glu Val Ala Lys Lys Glu Asp Lys Thr Pro Ile Lys Lys Glu
            660                 665                 670

Glu Lys Pro Lys Lys Glu Val Lys Lys Val Lys Lys Glu Ile
        675                 680                 685

Lys Lys Glu Glu Lys Lys Glu Pro Lys Lys Glu Val Lys Lys Glu Thr
690                 695                 700

Pro Pro Lys Glu Val Lys Lys Glu Val Lys Lys Glu Lys Lys Glu
705                 710                 715                 720

Val Lys Lys Glu Glu Lys Glu Pro Lys Lys Glu Ile Lys Lys Leu Pro
                725                 730                 735

Lys Asp Ala Lys Lys Ser Ser Thr Pro Leu Ser Glu Ala Lys Lys Pro
            740                 745                 750

Ala Ala Leu Lys Pro Lys Val Pro Lys Lys Glu Glu Ser Val Lys Lys
        755                 760                 765

Asp Ser Val Ala Ala Gly Lys Pro Lys Glu Lys Gly Lys Ile Lys Val
    770                 775                 780

Ile Lys Lys Glu Gly Lys Ala Ala Glu Ala Val Ala Ala Ala Val Gly
785                 790                 795                 800

Thr Gly Ala Thr Thr Ala Ala Val Met Ala Ala Ala Gly Ile Ala Ala
                805                 810                 815

Ile Gly Pro Ala Lys Glu Leu Glu Ala Glu Arg Ser Leu Met Ser Ser
            820                 825                 830

Pro Glu Asp Leu Thr Lys Asp Phe Glu Glu Leu Lys Ala Glu Glu Val
        835                 840                 845

Asp Val Thr Lys Asp Ile Lys Pro Gln Leu Glu Leu Ile Glu Asp Glu
    850                 855                 860

Glu Lys Leu Lys Glu Thr Glu Pro Val Glu Ala Tyr Val Ile Gln Lys
865                 870                 875                 880

Glu Arg Glu Val Thr Lys Gly Pro Ala Glu Ser Pro Asp Glu Gly Ile
                885                 890                 895

Thr Thr Thr Glu Gly Glu Gly Glu Cys Glu Gln Thr Pro Glu Glu Leu
            900                 905                 910

Glu Pro Val Glu Lys Gln Gly Val Asp Asp Ile Glu Lys Phe Glu Asp
        915                 920                 925

Glu Gly Ala Gly Phe Glu Glu Ser Ser Glu Thr Gly Asp Tyr Glu Glu
    930                 935                 940

Lys Ala Glu Thr Glu Glu Ala Glu Glu Pro Glu Glu Asp Gly Glu Glu
945                 950                 955                 960
```

His Val Cys Val Ser Ala Ser Lys His Ser Pro Thr Glu Asp Glu Glu
            965                 970                 975

Ser Ala Lys Ala Glu Ala Asp Ala Tyr Ile Arg Glu Lys Arg Glu Ser
            980                 985                 990

Val Ala Ser Gly Asp Asp Arg Ala  Glu Glu Asp Met Asp  Glu Ala Ile
            995                 1000                1005

Glu Lys Gly Glu Ala Glu Gln  Ser Glu Glu Ala  Asp Glu Glu
      1010               1015               1020

Asp Lys Ala Glu Asp Ala Arg  Glu Glu Glu Tyr  Glu Pro Glu Lys
      1025               1030               1035

Met Glu Ala Glu Asp Tyr Val  Met Ala Val Val  Asp Lys Ala Ala
      1040               1045               1050

Glu Ala Gly Gly Ala Glu Glu  Gln Tyr Gly Phe Leu  Thr Thr Pro
      1055               1060               1065

Thr Lys Gln Leu Gly Ala Gln  Ser Pro Gly Arg Glu  Pro Ala Ser
      1070               1075               1080

Ser Ile His Asp Glu Thr Leu  Pro Gly Gly Ser Glu  Ser Glu Ala
      1085               1090               1095

Thr Ala Ser Asp Glu Glu Asn  Arg Glu Asp Gln Pro  Glu Glu Phe
      1100               1105               1110

Thr Ala Thr Ser Gly Tyr Thr  Gln Ser Thr Ile Glu  Ile Ser Ser
      1115               1120               1125

Glu Pro Thr Pro Met Asp Glu  Met Ser Thr Pro Arg  Asp Val Met
      1130               1135               1140

Ser Asp Glu Thr Asn Asn Glu  Glu Thr Glu Ser Pro  Ser Gln Glu
      1145               1150               1155

Phe Val Asn Ile Thr Lys Tyr  Glu Ser Ser Leu Tyr  Ser Gln Glu
      1160               1165               1170

Tyr Ser Lys Pro Ala Asp Val  Thr Pro Leu Asn Gly  Phe Ser Glu
      1175               1180               1185

Gly Ser Lys Thr Asp Ala Thr  Asp Gly Lys Asp Tyr  Asn Ala Ser
      1190               1195               1200

Ala Ser Thr Ile Ser Pro Pro  Ser Ser Met Glu Glu  Asp Lys Phe
      1205               1210               1215

Ser Arg Ser Ala Leu Arg Asp  Ala Tyr Cys Ser Glu  Val Lys Ala
      1220               1225               1230

Ser Thr Thr Leu Asp Ile Lys  Asp Ser Ile Ser Ala  Val Ser Ser
      1235               1240               1245

Glu Lys Val Ser Pro Ser Lys  Ser Pro Ser Leu Ser  Pro Ser Pro
      1250               1255               1260

Pro Ser Pro Leu Glu Lys Thr  Pro Leu Gly Glu Arg  Ser Val Asn
      1265               1270               1275

Phe Ser Leu Thr Pro Asn Glu  Ile Lys Val Ser Ala  Glu Ala Glu
      1280               1285               1290

Val Ala Pro Val Ser Pro Glu  Val Thr Gln Glu Val  Val Glu Glu
      1295               1300               1305

His Cys Ala Ser Pro Glu Asp  Lys Thr Leu Glu Val  Val Ser Pro
      1310               1315               1320

Ser Gln Ser Val Thr Gly Ser  Ala Gly His Thr Pro  Tyr Tyr Gln
      1325               1330               1335

Ser Pro Thr Asp Glu Lys Ser  Ser His Leu Pro Thr  Glu Val Ile
      1340               1345               1350

Glu Lys Pro Pro Ala Val Pro  Val Ser Phe Glu Phe  Ser Asp Ala

-continued

|     |     |     |
| --- | --- | --- |
| 1355 | 1360 | 1365 |

Lys Asp Glu Asn Glu Arg Ala Ser Val Ser Pro Met Asp Glu Pro
1370            1375            1380

Val Pro Asp Ser Glu Ser Pro Ile Glu Lys Val Leu Ser Pro Leu
1385            1390            1395

Arg Ser Pro Pro Leu Ile Gly Ser Glu Ser Ala Tyr Glu Ser Phe
1400            1405            1410

Leu Ser Ala Asp Asp Lys Ala Ser Gly Arg Gly Ala Glu Ser Pro
1415            1420            1425

Phe Glu Glu Lys Ser Gly Lys Gln Gly Ser Pro Asp Gln Val Ser
1430            1435            1440

Pro Val Ser Glu Met Thr Ser Thr Ser Leu Tyr Gln Asp Lys Gln
1445            1450            1455

Glu Gly Lys Ser Thr Asp Phe Ala Pro Ile Lys Glu Asp Phe Gly
1460            1465            1470

Gln Glu Lys Lys Thr Asp Asp Val Glu Ala Met Ser Ser Gln Pro
1475            1480            1485

Ala Leu Ala Leu Asp Glu Arg Lys Leu Gly Asp Val Ser Pro Thr
1490            1495            1500

Gln Ile Asp Val Ser Gln Phe Gly Ser Phe Lys Glu Asp Thr Lys
1505            1510            1515

Met Ser Ile Ser Glu Gly Thr Val Ser Asp Lys Ser Ala Thr Pro
1520            1525            1530

Val Asp Glu Gly Val Ala Glu Asp Thr Tyr Ser His Met Glu Gly
1535            1540            1545

Val Ala Ser Val Ser Thr Ala Ser Val Ala Thr Ser Ser Phe Pro
1550            1555            1560

Glu Pro Thr Thr Asp Asp Val Ser Pro Ser Leu His Ala Glu Val
1565            1570            1575

Gly Ser Pro His Ser Thr Glu Val Asp Asp Ser Leu Ser Val Ser
1580            1585            1590

Val Val Gln Thr Pro Thr Thr Phe Gln Glu Thr Glu Met Ser Pro
1595            1600            1605

Ser Lys Glu Glu Cys Pro Arg Pro Met Ser Ile Ser Pro Pro Asp
1610            1615            1620

Phe Ser Pro Lys Thr Ala Lys Ser Arg Thr Pro Val Gln Asp His
1625            1630            1635

Arg Ser Glu Gln Ser Ser Met Ser Ile Glu Phe Gly Gln Glu Ser
1640            1645            1650

Pro Glu Gln Ser Leu Ala Met Asp Phe Ser Arg Gln Ser Pro Asp
1655            1660            1665

His Pro Thr Val Gly Ala Gly Val Leu His Ile Thr Glu Asn Gly
1670            1675            1680

Pro Thr Glu Val Asp Tyr Ser Pro Ser Asp Met Gln Asp Ser Ser
1685            1690            1695

Leu Ser His Lys Ile Pro Pro Met Glu Glu Pro Ser Tyr Thr Gln
1700            1705            1710

Asp Asn Asp Leu Ser Glu Leu Ile Ser Val Ser Gln Val Glu Ala
1715            1720            1725

Ser Pro Ser Thr Ser Ser Ala His Thr Pro Ser Gln Ile Ala Ser
1730            1735            1740

Pro Leu Gln Glu Asp Thr Leu Ser Asp Val Ala Pro Pro Arg Asp
1745            1750            1755

Met Ser Leu Tyr Ala Ser Leu Thr Ser Glu Lys Val Gln Ser Leu
1760                1765                1770

Glu Gly Glu Lys Leu Ser Pro Lys Ser Asp Ile Ser Pro Leu Thr
1775                1780                1785

Pro Arg Glu Ser Ser Pro Leu Tyr Ser Pro Thr Phe Ser Asp Ser
1790                1795                1800

Thr Ser Ala Val Lys Glu Lys Thr Ala Thr Cys His Ser Ser Ser
1805                1810                1815

Ser Pro Pro Ile Asp Ala Ala Ser Ala Glu Pro Tyr Gly Phe Arg
1820                1825                1830

Ala Ser Val Leu Phe Asp Thr Met Gln His His Leu Ala Leu Asn
1835                1840                1845

Arg Asp Leu Ser Thr Pro Gly Leu Glu Lys Asp Ser Gly Gly Lys
1850                1855                1860

Thr Pro Gly Asp Phe Ser Tyr Ala Tyr Gln Lys Pro Glu Glu Thr
1865                1870                1875

Thr Arg Ser Pro Asp Glu Glu Asp Tyr Asp Tyr Glu Ser Tyr Glu
1880                1885                1890

Lys Thr Thr Arg Thr Ser Asp Val Gly Gly Tyr Tyr Tyr Glu Lys
1895                1900                1905

Ile Glu Arg Thr Thr Lys Ser Pro Ser Asp Ser Gly Tyr Ser Tyr
1910                1915                1920

Glu Thr Ile Gly Lys Thr Thr Lys Thr Pro Glu Asp Gly Asp Tyr
1925                1930                1935

Ser Tyr Glu Ile Ile Glu Lys Thr Thr Arg Thr Pro Glu Glu Gly
1940                1945                1950

Gly Tyr Ser Tyr Asp Ile Ser Glu Lys Thr Thr Ser Pro Pro Glu
1955                1960                1965

Val Ser Gly Tyr Ser Tyr Glu Lys Thr Glu Arg Ser Arg Arg Leu
1970                1975                1980

Leu Asp Asp Ile Ser Asn Gly Tyr Asp Asp Ser Glu Asp Gly Gly
1985                1990                1995

His Thr Leu Gly Asp Pro Ser Tyr Ser Tyr Glu Thr Thr Glu Lys
2000                2005                2010

Ile Thr Ser Phe Pro Glu Ser Glu Gly Tyr Ser Tyr Glu Thr Ser
2015                2020                2025

Thr Lys Thr Thr Arg Thr Pro Asp Thr Ser Thr Tyr Cys Tyr Glu
2030                2035                2040

Thr Ala Glu Lys Ile Thr Arg Thr Pro Gln Ala Ser Thr Tyr Ser
2045                2050                2055

Tyr Glu Thr Ser Asp Leu Cys Tyr Thr Ala Glu Lys Lys Ser Pro
2060                2065                2070

Ser Glu Ala Arg Gln Asp Val Asp Leu Cys Leu Val Ser Ser Cys
2075                2080                2085

Glu Tyr Lys His Pro Lys Thr Glu Leu Ser Pro Ser Phe Ile Asn
2090                2095                2100

Pro Asn Pro Leu Glu Trp Phe Ala Ser Glu Glu Pro Thr Glu Glu
2105                2110                2115

Ser Glu Lys Pro Leu Thr Gln Ser Gly Gly Ala Pro Pro Pro Pro
2120                2125                2130

Gly Gly Lys Gln Gln Gly Arg Gln Cys Asp Glu Thr Pro Pro Thr
2135                2140                2145

```
Ser Val Ser Glu Ser Ala Pro Ser Gln Thr Asp Ser Asp Val Pro
    2150                2155                2160

Pro Glu Thr Glu Glu Cys Pro Ser Ile Thr Ala Asp Ala Asn Ile
    2165                2170                2175

Asp Ser Glu Asp Glu Ser Glu Thr Ile Pro Thr Asp Lys Thr Val
    2180                2185                2190

Thr Tyr Lys His Met Asp Pro Pro Ala Pro Val Gln Asp Arg
    2195                2200                2205

Ser Pro Ser Pro Arg His Pro Asp Val Ser Met Val Asp Pro Glu
    2210                2215                2220

Ala Leu Ala Ile Glu Gln Asn Leu Gly Lys Ala Leu Lys Lys Asp
    2225                2230                2235

Leu Lys Glu Lys Thr Lys Thr Lys Lys Pro Gly Thr Lys Thr Lys
    2240                2245                2250

Ser Ser Ser Pro Val Lys Lys Ser Asp Gly Lys Ser Lys Pro Leu
    2255                2260                2265

Ala Ala Ser Pro Lys Pro Ala Gly Leu Lys Glu Ser Ser Asp Lys
    2270                2275                2280

Val Ser Arg Val Ala Ser Pro Lys Lys Lys Glu Ser Val Glu Lys
    2285                2290                2295

Ala Ala Lys Pro Thr Thr Thr Pro Glu Val Lys Ala Ala Arg Gly
    2300                2305                2310

Glu Glu Lys Asp Lys Glu Thr Lys Asn Ala Ala Asn Ala Ser Ala
    2315                2320                2325

Ser Lys Ser Ala Lys Thr Ala Thr Ala Gly Pro Gly Thr Thr Lys
    2330                2335                2340

Thr Thr Lys Ser Ser Ala Val Pro Pro Gly Leu Pro Val Tyr Leu
    2345                2350                2355

Asp Leu Cys Tyr Ile Pro Asn His Ser Asn Ser Lys Asn Val Asp
    2360                2365                2370

Val Glu Phe Phe Lys Arg Val Arg Ser Ser Tyr Tyr Val Val Ser
    2375                2380                2385

Gly Asn Asp Pro Ala Ala Glu Glu Pro Ser Arg Ala Val Leu Asp
    2390                2395                2400

Ala Leu Leu Glu Gly Lys Ala Gln Trp Gly Ser Asn Met Gln Val
    2405                2410                2415

Thr Leu Ile Pro Thr His Asp Ser Glu Val Met Arg Glu Trp Tyr
    2420                2425                2430

Gln Glu Thr His Glu Lys Gln Gln Asp Leu Asn Ile Met Val Leu
    2435                2440                2445

Ala Ser Ser Ser Thr Val Val Met Gln Asp Glu Ser Phe Pro Ala
    2450                2455                2460

Cys Lys Ile Glu Leu
    2465

<210> SEQ ID NO 2
<211> LENGTH: 2803
<212> TYPE: PRT
<213> ORGANISM: Homo sapiens

<400> SEQUENCE: 2

Met Asp Gly Val Ala Glu Phe Ser Glu Tyr Val Ser Glu Thr Val Asp
1               5                   10                  15

Val Pro Ser Pro Phe Asp Leu Leu Glu Pro Pro Thr Ser Gly Gly Phe
            20                  25                  30
```

```
Leu Lys Leu Ser Lys Pro Cys Cys Tyr Ile Phe Pro Gly Gly Arg Gly
         35                  40                  45

Asp Ser Ala Leu Phe Ala Val Asn Gly Phe Asn Ile Leu Val Asp Gly
 50                  55                  60

Gly Ser Asp Arg Lys Ser Cys Phe Trp Lys Leu Val Arg His Leu Asp
 65                  70                  75                  80

Arg Ile Asp Ser Val Leu Leu Thr His Ile Gly Ala Asp Asn Leu Pro
                 85                  90                  95

Gly Ile Asn Gly Leu Leu Gln Arg Lys Val Ala Glu Leu Glu Glu Glu
                100                 105                 110

Gln Ser Gln Gly Ser Ser Tyr Ser Asp Trp Val Lys Asn Leu Ile
        115                 120                 125

Ser Pro Glu Leu Gly Val Val Phe Phe Asn Val Pro Glu Lys Leu Arg
        130                 135                 140

Leu Pro Asp Ala Ser Arg Lys Ala Lys Arg Ser Ile Glu Glu Ala Cys
145                 150                 155                 160

Leu Thr Leu Gln His Leu Asn Arg Leu Gly Ile Gln Ala Glu Pro Leu
                165                 170                 175

Tyr Arg Val Val Ser Asn Thr Ile Glu Pro Leu Thr Leu Phe His Lys
            180                 185                 190

Met Gly Val Gly Arg Leu Asp Met Tyr Val Leu Asn Pro Val Lys Asp
            195                 200                 205

Ser Lys Glu Met Gln Phe Leu Met Gln Lys Trp Ala Gly Asn Ser Lys
        210                 215                 220

Ala Lys Thr Gly Ile Val Leu Pro Asn Gly Lys Glu Ala Glu Ile Ser
225                 230                 235                 240

Val Pro Tyr Leu Thr Ser Ile Thr Ala Leu Val Val Trp Leu Pro Ala
                245                 250                 255

Asn Pro Thr Glu Lys Ile Val Arg Val Leu Phe Pro Gly Asn Ala Pro
                260                 265                 270

Gln Asn Lys Ile Leu Glu Gly Leu Glu Lys Leu Arg His Leu Asp Phe
        275                 280                 285

Leu Arg Tyr Pro Val Ala Thr Gln Lys Asp Leu Ala Ser Gly Ala Val
        290                 295                 300

Pro Thr Asn Leu Lys Pro Ser Lys Ile Lys Gln Arg Ala Asp Ser Lys
305                 310                 315                 320

Glu Ser Leu Lys Ala Thr Thr Lys Thr Ala Val Ser Lys Leu Ala Lys
                325                 330                 335

Arg Glu Glu Val Val Glu Gly Ala Lys Glu Ala Arg Ser Glu Leu
                340                 345                 350

Ala Lys Glu Leu Ala Lys Thr Glu Lys Lys Ala Lys Glu Ser Ser Glu
        355                 360                 365

Lys Pro Pro Glu Lys Pro Ala Lys Pro Glu Arg Val Lys Thr Glu Ser
370                 375                 380

Ser Glu Ala Leu Lys Ala Glu Lys Arg Lys Leu Ile Lys Asp Lys Val
385                 390                 395                 400

Gly Lys Lys His Leu Lys Glu Lys Ile Ser Lys Leu Glu Glu Lys Lys
                405                 410                 415

Asp Lys Glu Lys Lys Glu Ile Lys Lys Glu Arg Lys Glu Leu Lys Lys
            420                 425                 430

Asp Glu Gly Arg Lys Glu Lys Lys Asp Ala Lys Lys Glu Glu Lys
        435                 440                 445
```

-continued

| | | | | | | | | | | | | | | |
|---|---|---|---|---|---|---|---|---|---|---|---|---|---|---|
|Arg|Lys|Asp|Thr|Lys|Pro|Glu|Leu|Lys|Lys|Ile|Ser|Lys|Pro|Asp|Leu|
| |450| | | |455| | | |460| | | | | |

Lys Pro Phe Thr Pro Glu Val Arg Lys Thr Leu Tyr Lys Ala Lys Val
465                 470                 475                 480

Pro Gly Arg Val Lys Ile Asp Arg Ser Arg Ala Ile Arg Gly Glu Lys
                485                 490                 495

Glu Leu Ser Ser Glu Pro Gln Thr Pro Pro Ala Gln Lys Gly Thr Val
            500                 505                 510

Pro Leu Pro Thr Ile Ser Gly His Arg Glu Leu Val Leu Ser Ser Pro
        515                 520                 525

Glu Asp Leu Thr Gln Asp Phe Glu Glu Met Lys Arg Glu Glu Arg Ala
    530                 535                 540

Leu Leu Ala Glu Gln Arg Asp Thr Gly Leu Gly Asp Lys Pro Phe Pro
545                 550                 555                 560

Leu Asp Thr Ala Glu Glu Gly Pro Pro Ser Thr Ala Ile Gln Gly Thr
                565                 570                 575

Pro Pro Ser Val Pro Gly Leu Gly Gln Glu Glu His Val Met Lys Glu
            580                 585                 590

Lys Glu Leu Val Pro Glu Val Pro Glu Glu Gln Gly Ser Lys Asp Arg
        595                 600                 605

Gly Leu Asp Ser Gly Ala Glu Thr Glu Glu Lys Asp Thr Trp Glu
    610                 615                 620

Glu Lys Lys Gln Arg Glu Ala Glu Arg Leu Pro Asp Arg Thr Glu Ala
625                 630                 635                 640

Arg Glu Glu Ser Glu Pro Glu Val Lys Glu Asp Val Ile Glu Lys Ala
                645                 650                 655

Glu Leu Glu Glu Met Glu Glu Val His Pro Ser Asp Glu Glu Glu
            660                 665                 670

Asp Ala Thr Lys Ala Glu Gly Phe Tyr Gln Lys His Met Gln Glu Pro
        675                 680                 685

Leu Lys Val Thr Pro Arg Ser Arg Glu Ala Phe Gly Gly Arg Glu Leu
    690                 695                 700

Gly Leu Gln Gly Lys Ala Pro Glu Lys Glu Thr Ser Leu Phe Leu Ser
705                 710                 715                 720

Ser Leu Thr Thr Pro Ala Gly Ala Thr Glu His Val Ser Tyr Ile Gln
                725                 730                 735

Asp Glu Thr Ile Pro Gly Tyr Ser Glu Thr Glu Gln Thr Ile Ser Asp
            740                 745                 750

Glu Glu Ile His Asp Glu Pro Glu Arg Pro Ala Pro Arg Phe
        755                 760                 765

His Thr Ser Thr Tyr Asp Leu Pro Gly Pro Glu Gly Ala Gly Pro Phe
    770                 775                 780

Glu Ala Ser Gln Pro Ala Asp Ser Ala Val Pro Ala Thr Ser Gly Lys
785                 790                 795                 800

Val Tyr Gly Thr Pro Glu Thr Glu Leu Thr Tyr Pro Thr Asn Ile Val
                805                 810                 815

Ala Ala Pro Leu Ala Glu Glu His Val Ser Ser Ala Thr Ser Ile
            820                 825                 830

Thr Glu Cys Asp Lys Leu Ser Ser Phe Ala Thr Ser Val Ala Glu Asp
        835                 840                 845

Gln Ser Val Ala Ser Leu Thr Ala Pro Gln Thr Glu Glu Thr Gly Lys
    850                 855                 860

Ser Ser Leu Leu Leu Asp Thr Val Thr Ser Ile Pro Ser Ser Arg Thr

-continued

```
865                 870                 875                 880
Glu Ala Thr Gln Gly Leu Asp Tyr Val Pro Ser Ala Gly Thr Ile Ser
                885                 890                 895
Pro Thr Ser Ser Leu Glu Glu Asp Lys Gly Phe Lys Ser Pro Pro Cys
                900                 905                 910
Glu Asp Phe Ser Val Thr Gly Glu Ser Glu Lys Arg Gly Glu Ile Ile
                915                 920                 925
Gly Lys Gly Leu Ser Gly Glu Arg Ala Val Glu Glu Glu Glu Glu Glu
            930                 935                 940
Thr Ala Asn Val Glu Met Ser Glu Lys Leu Cys Ser Gln Tyr Gly Thr
945                 950                 955                 960
Pro Val Phe Ser Ala Pro Gly His Ala Leu His Pro Gly Glu Pro Ala
                965                 970                 975
Leu Gly Glu Ala Glu Glu Arg Cys Leu Ser Pro Asp Asp Ser Thr Val
                980                 985                 990
Lys Met Ala Ser Pro Pro Pro Ser  Gly Pro Pro Ser Ala  Thr His Thr
                995                 1000                1005
Pro Phe  His Gln Ser Pro Val  Glu Glu Lys Ser Glu  Pro Gln Asp
     1010                1015                1020
Phe Gln  Glu Ala Asp Ser Trp  Gly Asp Thr Lys Arg  Thr Pro Gly
     1025                1030                1035
Val Gly  Lys Glu Asp Ala Ala  Glu Glu Thr Val Lys  Pro Gly Pro
     1040                1045                1050
Glu Glu  Gly Thr Leu Glu Lys  Glu Glu Lys Val Pro  Pro Pro Arg
     1055                1060                1065
Ser Pro  Gln Ala Gln Glu Ala  Pro Val Asn Ile Asp  Glu Gly Leu
     1070                1075                1080
Thr Gly  Cys Thr Ile Gln Leu  Leu Pro Ala Gln Asp  Lys Ala Ile
     1085                1090                1095
Val Phe  Glu Ile Met Glu Ala  Gly Glu Pro Thr Gly  Pro Ile Leu
     1100                1105                1110
Gly Ala  Glu Ala Leu Pro Gly  Gly Leu Arg Thr Leu  Pro Gln Glu
     1115                1120                1125
Pro Gly  Lys Pro Gln Lys Asp  Glu Val Leu Arg Tyr  Pro Asp Arg
     1130                1135                1140
Ser Leu  Ser Pro Glu Asp Ala  Glu Ser Leu Ser Val  Leu Ser Val
     1145                1150                1155
Pro Ser  Pro Asp Thr Ala Asn  Gln Glu Pro Thr Pro  Lys Ser Pro
     1160                1165                1170
Cys Gly  Leu Thr Glu Gln Tyr  Leu His Lys Asp Arg  Trp Pro Glu
     1175                1180                1185
Val Ser  Pro Glu Asp Thr Gln  Ser Leu Ser Leu Ser  Glu Glu Ser
     1190                1195                1200
Pro Ser  Lys Glu Thr Ser Leu  Asp Val Ser Ser Lys  Gln Leu Ser
     1205                1210                1215
Pro Glu  Ser Leu Gly Thr Leu  Gln Phe Gly Glu Leu  Asn Leu Gly
     1220                1225                1230
Lys Glu  Glu Met Gly His Leu  Met Gln Ala Glu Asp  Thr Ser His
     1235                1240                1245
His Thr  Ala Pro Met Ser Val  Pro Glu Pro His Ala  Ala Thr Ala
     1250                1255                1260
Ser Pro  Pro Thr Asp Gly Thr  Thr Arg Tyr Ser Ala  Gln Thr Asp
     1265                1270                1275
```

```
Ile Thr Asp Asp Ser Leu Asp Arg Lys Ser Pro Ala Ser Ser Phe
    1280            1285            1290

Ser His Ser Thr Pro Ser Gly Asn Gly Lys Tyr Leu Pro Gly Ala
    1295            1300            1305

Ile Thr Ser Pro Asp Glu His Ile Leu Thr Pro Asp Ser Ser Phe
    1310            1315            1320

Ser Lys Ser Pro Glu Ser Leu Pro Gly Pro Ala Leu Glu Asp Ile
    1325            1330            1335

Ala Ile Lys Trp Glu Asp Lys Val Pro Gly Leu Lys Asp Arg Thr
    1340            1345            1350

Ser Glu Gln Lys Lys Glu Pro Glu Pro Lys Asp Glu Val Leu Gln
    1355            1360            1365

Gln Lys Asp Lys Thr Leu Glu His Lys Glu Val Val Glu Pro Lys
    1370            1375            1380

Asp Thr Ala Ile Tyr Gln Lys Asp Glu Ala Leu His Val Lys Asn
    1385            1390            1395

Glu Ala Val Lys Gln Gln Asp Lys Ala Leu Glu Gln Lys Gly Arg
    1400            1405            1410

Asp Leu Glu Gln Lys Asp Thr Ala Leu Glu Gln Lys Asp Lys Ala
    1415            1420            1425

Leu Glu Pro Lys Asp Lys Asp Leu Glu Glu Lys Asp Lys Ala Leu
    1430            1435            1440

Glu Gln Lys Asp Lys Ile Pro Glu Glu Lys Asp Lys Ala Leu Glu
    1445            1450            1455

Gln Lys Asp Thr Ala Leu Glu Gln Lys Asp Lys Ala Leu Glu Pro
    1460            1465            1470

Lys Asp Lys Asp Leu Glu Gln Lys Asp Arg Val Leu Glu Gln Lys
    1475            1480            1485

Glu Lys Ile Pro Glu Glu Lys Asp Lys Ala Leu Asp Gln Lys Val
    1490            1495            1500

Arg Ser Val Glu His Lys Ala Pro Glu Asp Thr Val Ala Glu Met
    1505            1510            1515

Lys Asp Arg Asp Leu Glu Gln Thr Asp Lys Ala Pro Glu Gln Lys
    1520            1525            1530

His Gln Ala Gln Glu Gln Lys Asp Lys Val Ser Glu Lys Lys Asp
    1535            1540            1545

Gln Ala Leu Glu Gln Lys Tyr Trp Ala Leu Gly Gln Lys Asp Glu
    1550            1555            1560

Ala Leu Glu Gln Asn Ile Gln Ala Leu Glu Glu Asn His Gln Thr
    1565            1570            1575

Gln Glu Gln Glu Ser Leu Val Gln Glu Asp Lys Thr Arg Lys Pro
    1580            1585            1590

Lys Met Leu Glu Glu Lys Ser Pro Glu Lys Val Lys Ala Met Glu
    1595            1600            1605

Glu Lys Leu Glu Ala Leu Leu Glu Lys Thr Lys Ala Leu Gly Leu
    1610            1615            1620

Glu Glu Ser Leu Val Gln Glu Gly Arg Ala Arg Glu Gln Glu Glu
    1625            1630            1635

Lys Tyr Trp Arg Gly Gln Asp Val Val Gln Glu Trp Gln Glu Thr
    1640            1645            1650

Ser Pro Thr Arg Glu Glu Pro Ala Gly Glu Gln Lys Glu Leu Ala
    1655            1660            1665
```

```
Pro Ala Trp Glu Asp Thr Ser Pro Glu Gln Asp Asn Arg Tyr Trp
    1670                1675                1680

Arg Gly Arg Glu Asp Val Ala Leu Glu Gln Asp Thr Tyr Trp Arg
    1685                1690                1695

Glu Leu Ser Cys Glu Arg Lys Val Trp Phe Pro His Glu Leu Asp
    1700                1705                1710

Gly Gln Gly Ala Arg Pro His Tyr Thr Glu Arg Glu Ser Thr
    1715                1720                1725

Phe Leu Asp Glu Gly Pro Asp Glu Gln Glu Val Pro Leu Arg
    1730                1735                1740

Glu His Ala Thr Arg Ser Pro Trp Ala Ser Asp Phe Lys Asp Phe
    1745                1750                1755

Gln Glu Ser Ser Pro Gln Lys Gly Leu Glu Val Glu Arg Trp Leu
    1760                1765                1770

Ala Glu Ser Pro Val Gly Leu Pro Pro Glu Glu Glu Asp Lys Leu
    1775                1780                1785

Thr Arg Ser Pro Phe Glu Ile Ile Ser Pro Pro Ala Ser Pro Pro
    1790                1795                1800

Glu Met Val Gly Gln Arg Val Pro Ser Ala Pro Gly Gln Glu Ser
    1805                1810                1815

Pro Ile Pro Asp Pro Lys Leu Met Pro His Met Lys Asn Glu Pro
    1820                1825                1830

Thr Thr Pro Ser Trp Leu Ala Asp Ile Pro Pro Trp Val Pro Lys
    1835                1840                1845

Asp Arg Pro Leu Pro Pro Ala Pro Leu Ser Pro Ala Pro Gly Pro
    1850                1855                1860

Pro Thr Pro Ala Pro Glu Ser His Thr Pro Ala Pro Phe Ser Trp
    1865                1870                1875

Gly Thr Ala Glu Tyr Asp Ser Val Val Ala Ala Val Gln Glu Gly
    1880                1885                1890

Ala Ala Glu Leu Glu Gly Gly Pro Tyr Ser Pro Leu Gly Lys Asp
    1895                1900                1905

Tyr Arg Lys Ala Glu Gly Glu Arg Glu Glu Gly Arg Ala Glu
    1910                1915                1920

Ala Pro Asp Lys Ser Ser His Ser Ser Lys Val Pro Glu Ala Ser
    1925                1930                1935

Lys Ser His Ala Thr Thr Glu Pro Gln Thr Glu Pro Glu Gln
    1940                1945                1950

Arg Glu Pro Thr Pro Tyr Pro Asp Glu Arg Ser Phe Gln Tyr Ala
    1955                1960                1965

Asp Ile Tyr Glu Gln Met Met Leu Thr Gly Leu Gly Pro Ala Cys
    1970                1975                1980

Pro Thr Arg Glu Pro Pro Leu Gly Ala Ala Gly Asp Trp Pro Pro
    1985                1990                1995

Cys Leu Ser Thr Lys Glu Ala Ala Ala Gly Arg Asn Thr Ser Ala
    2000                2005                2010

Glu Lys Glu Leu Ser Ser Pro Ile Ser Pro Lys Ser Leu Gln Ser
    2015                2020                2025

Asp Thr Pro Thr Phe Ser Tyr Ala Ala Leu Ala Gly Pro Thr Val
    2030                2035                2040

Pro Pro Arg Pro Glu Pro Gly Pro Ser Met Glu Pro Ser Leu Thr
    2045                2050                2055

Pro Pro Ala Val Pro Pro Arg Ala Pro Ile Leu Ser Lys Gly Pro
```

-continued

|   |   |   | 2060 |   |   |   | 2065 |   |   |   | 2070 |   |   |
|---|---|---|---|---|---|---|---|---|---|---|---|---|---|

Ser Pro Pro Leu Asn Gly Asn Ile Leu Ser Cys Ser Pro Asp Arg
    2075                2080                2085

Arg Ser Pro Ser Pro Lys Glu Ser Gly Arg Ser His Trp Asp Asp
    2090                2095                2100

Ser Thr Ser Asp Ser Glu Leu Glu Lys Gly Ala Arg Glu Gln Pro
    2105                2110                2115

Glu Lys Glu Ala Gln Ser Pro Ser Pro Pro His Pro Ile Pro Met
    2120                2125                2130

Gly Ser Pro Thr Leu Trp Pro Glu Thr Glu Ala His Val Ser Pro
    2135                2140                2145

Pro Leu Asp Ser His Leu Gly Pro Ala Arg Pro Ser Leu Asp Phe
    2150                2155                2160

Pro Ala Ser Ala Phe Gly Phe Ser Ser Leu Gln Pro Ala Pro Pro
    2165                2170                2175

Gln Leu Pro Ser Pro Ala Glu Pro Arg Ser Ala Pro Cys Gly Ser
    2180                2185                2190

Leu Ala Phe Ser Gly Asp Arg Ala Leu Ala Leu Ala Pro Gly Pro
    2195                2200                2205

Pro Thr Arg Thr Arg His Asp Glu Tyr Leu Glu Val Thr Lys Ala
    2210                2215                2220

Pro Ser Leu Asp Ser Ser Leu Pro Gln Leu Pro Ser Pro Ser Ser
    2225                2230                2235

Pro Gly Ala Pro Leu Leu Ser Asn Leu Pro Arg Pro Ala Ser Pro
    2240                2245                2250

Ala Leu Ser Glu Gly Ser Ser Ser Glu Ala Thr Thr Pro Val Ile
    2255                2260                2265

Ser Ser Val Ala Glu Arg Phe Ser Pro Ser Leu Glu Ala Ala Glu
    2270                2275                2280

Gln Glu Ser Gly Glu Leu Asp Pro Gly Met Glu Pro Ala Ala His
    2285                2290                2295

Ser Leu Trp Asp Leu Thr Pro Leu Ser Pro Ala Pro Pro Ala Ser
    2300                2305                2310

Leu Asp Leu Ala Leu Ala Pro Ala Pro Ser Leu Pro Gly Asp Met
    2315                2320                2325

Gly Asp Gly Ile Leu Pro Cys His Leu Glu Cys Ser Glu Ala Ala
    2330                2335                2340

Thr Glu Lys Pro Ser Pro Phe Gln Val Pro Ser Glu Asp Cys Ala
    2345                2350                2355

Ala Asn Gly Pro Thr Glu Thr Ser Pro Asn Pro Pro Gly Pro Ala
    2360                2365                2370

Pro Ala Lys Ala Glu Asn Glu Glu Ala Ala Ala Cys Pro Ala Trp
    2375                2380                2385

Glu Arg Gly Ala Trp Pro Glu Gly Ala Glu Arg Ser Ser Arg Pro
    2390                2395                2400

Asp Thr Leu Leu Ser Pro Glu Gln Pro Val Cys Pro Ala Gly Gly
    2405                2410                2415

Ser Gly Gly Pro Pro Ser Ser Ala Ser Pro Glu Val Glu Ala Gly
    2420                2425                2430

Pro Gln Gly Cys Ala Thr Glu Pro Arg Pro His Arg Gly Glu Leu
    2435                2440                2445

Ser Pro Ser Phe Leu Asn Pro Pro Leu Pro Pro Ser Ile Asp Asp
    2450                2455                2460

-continued

```
Arg Asp Leu Ser Thr Glu Glu Val Arg Leu Val Gly Arg Gly Gly
    2465             2470                 2475
Arg Arg Arg Val Gly Gly Pro Gly Thr Thr Gly Gly Pro Cys Pro
    2480             2485                 2490
Val Thr Asp Glu Thr Pro Pro Thr Ser Ala Ser Asp Ser Gly Ser
    2495             2500                 2505
Ser Gln Ser Asp Ser Asp Val Pro Pro Glu Thr Glu Glu Cys Pro
    2510             2515                 2520
Ser Ile Thr Ala Glu Ala Ala Leu Asp Ser Asp Glu Asp Gly Asp
    2525             2530                 2535
Phe Leu Pro Val Asp Lys Ala Gly Gly Val Ser Gly Thr His His
    2540             2545                 2550
Pro Arg Pro Gly His Asp Pro Pro Pro Leu Pro Gln Pro Asp Pro
    2555             2560                 2565
Arg Pro Ser Pro Pro Arg Pro Asp Val Cys Met Ala Asp Pro Glu
    2570             2575                 2580
Gly Leu Ser Ser Glu Ser Gly Arg Val Glu Arg Leu Arg Glu Lys
    2585             2590                 2595
Glu Lys Val Gln Gly Arg Val Gly Arg Arg Ala Pro Gly Lys Ala
    2600             2605                 2610
Lys Pro Ala Ser Pro Ala Arg Arg Leu Asp Leu Arg Gly Lys Arg
    2615             2620                 2625
Ser Pro Thr Pro Gly Lys Gly Pro Ala Asp Arg Ala Ser Arg Ala
    2630             2635                 2640
Pro Pro Arg Pro Arg Ser Thr Thr Ser Gln Val Thr Pro Ala Glu
    2645             2650                 2655
Glu Lys Asp Gly His Ser Pro Met Ser Lys Gly Leu Val Asn Gly
    2660             2665                 2670
Leu Lys Ala Gly Pro Met Ala Leu Ser Ser Lys Gly Ser Ser Gly
    2675             2680                 2685
Ala Pro Val Tyr Val Asp Leu Ala Tyr Ile Pro Asn His Cys Ser
    2690             2695                 2700
Gly Lys Thr Ala Asp Leu Asp Phe Phe Arg Arg Val Arg Ala Ser
    2705             2710                 2715
Tyr Tyr Val Val Ser Gly Asn Asp Pro Ala Asn Gly Glu Pro Ser
    2720             2725                 2730
Arg Ala Val Leu Asp Ala Leu Leu Glu Gly Lys Ala Gln Trp Gly
    2735             2740                 2745
Glu Asn Leu Gln Val Thr Leu Ile Pro Thr His Asp Thr Glu Val
    2750             2755                 2760
Thr Arg Glu Trp Tyr Gln Gln Thr His Glu Gln Gln Gln Gln Leu
    2765             2770                 2775
Asn Val Leu Val Leu Ala Ser Ser Ser Thr Val Val Met Gln Asp
    2780             2785                 2790
Glu Ser Phe Pro Ala Cys Lys Ile Glu Phe
    2795             2800
```